US007259146B2

(12) United States Patent
Smith-Swintosky et al.

(10) Patent No.: US 7,259,146 B2
(45) Date of Patent: Aug. 21, 2007

(54) NEUROPROTECTIVE PEPTIDES

(75) Inventors: Virginia Smith-Swintosky, Hatfield, PA (US); Michael Renzi, Harleysville, PA (US); Carlos Plata-Salaman, Ambler, PA (US); Linda Jolliffe, Belle Mead, PA (US); Francis Farrell, Doylestown, PA (US); Dana Johnson, Upper Black Eddy, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/863,600

(22) Filed: May 23, 2001

(65) Prior Publication Data
US 2003/0130197 A1   Jul. 10, 2003

Related U.S. Application Data

(60) Provisional application No. 60/207,654, filed on May 26, 2000.

(51) Int. Cl.
*A61K 38/00* (2006.01)
*C07K 16/00* (2006.01)

(52) U.S. Cl. ............... 514/13; 514/15; 530/326; 530/327; 435/70.1

(58) Field of Classification Search ................ 514/16, 514/15, 14, 13, 12; 530/300, 328, 327, 326, 530/325, 324, 345
See application file for complete search history.

(56) References Cited

U.S. PATENT DOCUMENTS

| | | | | |
|---|---|---|---|---|
| 5,221,607 A | * | 6/1993 | Cordell et al. ............... 435/6 |
| 5,252,463 A | * | 10/1993 | Nelson et al. ................ 435/23 |
| 5,571,787 A | | 11/1996 | O'Brien et al. ............... 514/12 |
| 5,643,575 A | | 7/1997 | Martinez et al. ........... 424/194.1 |
| 5,688,679 A | | 11/1997 | Powell .................... 435/240.2 |
| 5,696,080 A | | 12/1997 | O'Brien et al. ............... 514/2 |
| 5,700,909 A | | 12/1997 | O'Brien .................... 520/326 |
| 5,714,459 A | | 2/1998 | O'Brien et al. ............... 514/2 |
| 5,767,078 A | * | 6/1998 | Johnson et al. .............. 514/12 |
| 5,773,569 A | * | 6/1998 | Wrighton et al. ............ 530/300 |
| 5,830,851 A | * | 11/1998 | Wrighton et al. ............. 514/2 |
| 5,986,047 A | | 11/1999 | Wrighton et al. ............ 530/300 |
| 6,165,783 A | * | 12/2000 | Weiss ....................... 435/325 |

FOREIGN PATENT DOCUMENTS

| | | |
|---|---|---|
| EP | 640619 | 7/1997 |
| WO | WO94/12650 | 6/1994 |
| WO | WO95/03821 | 6/1994 |
| WO | 96/40749 A1 | 12/1996 |
| WO | WO99/05268 | 2/1999 |
| WO | WO99/1781 | 3/1999 |
| WO | WO 99/21966 | 5/1999 |
| WO | WO99/21966 | * 5/1999 |
| WO | WO99/38890 | 8/1999 |
| WO | WO 00/24782 A | 5/2000 |
| WO | 04/100997 A2 | 5/2004 |
| WO | 04/101606 A2 | 11/2004 |
| WO | 04/101611 A2 | 11/2004 |

OTHER PUBLICATIONS

Ezzell, Scientific America, pp. 152-153, Mar. 7, 1993.*
Varon et al., Dev. Neurosci., vol. 6, pp. 73-100, 1983/1984.*
Johnson et al., Biochemistry, vol. 37, pp. 3699-3710, 1998.*
Campana et al., International Journal of Molecular Medicine, vol. 1, pp. 235-241, 1998.*
Bernaudin et al., Journal of Cerebral Blood Flow and Metabolism, vol. 19, pp. 643-651, 1999.*
Sakanaka et al., in vivo evidence that erythropoietin protects neurons from ischemic damage, Apr. 1998, Proc. Natl. Acad. Sci. USA, vol. 95, pp. 4635-4640.*
B. S. Beckman and M. Mason-Garcia, "Signal Transduction in Erythropoiesis", *The Faseb Journal* (1991) 5(14): 2958-2964).
Bernaudin et al., "A Potential Role for Erythropoietin in Focal Permanent Cerebral Ischemia in Mice", *J. Cereb. Blood Flow Metab.* (1999) 19:643-51.
Brint et al., "Focal Brain Ischemia in the Rat Methods for Reproducible Neocortical Infarction Using Tandem Occlusion of the Distal Middle Cerebral and Ipsilateral Common Cortoid Arteries", *J. Cereb. Blood Flow Metab.* (1988) 8(4):474-485.
Campana et al., "Identification of a Neurotrophic Sequence of Erythropoietin", *Inter. J. Mol. Med.* (1998) 1:235-241.
Eschbach et al., "Correction of the Anemia of End-stage Renal Disease with Recombinant Human Erythropoietin: Results of a Combined Phase I and II Clinical Trial", *New Engl. J. Med.* (1987) 316(2): 73-78.
Genc et al., "Erythropoietin Exerts Neuroprotection in 1-methyl-4-phenyl-1,2,3,6-tetrahydropyridin-treated C57/BL Mice Via Increasing Nitric Oxide Production", *Neuroscience Letters* (2001) 298:139-141.
Johnson et al., "Identification ofa 13 Amino Acid Peptide Mimeric of Erythropoietin and Description of Amino Acids Critical for the Mimetic Activity of EMP1", *Biochemistry* (1998) 37:3699-3710.
Johnson et al., "Amino-Terminal Dimerization of an Erythropoietin Mimetic Peptide Results in Increased Erythropoietic Activity", *Chemistry & Biology* (1997) 4(12):939-950.
Juul et al., "Immunohistochemical Localization of Erythropoietin and its Receptors in the Developing Human Brain", *Pediatr. Dev. Pathol.* (1999) 2(2):148-158.

(Continued)

Primary Examiner—Jon Weber
Assistant Examiner—Abdel A. Mohamed
(74) Attorney, Agent, or Firm—Yunling Ren

(57) ABSTRACT

Methods of treating diseases of the nervous system by administration of compositions having the neurological therapeutic activity of human erythropoietin are disclosed. These compositions include therapeutic agents such as peptides, peptide dimers, polypeptides, and proteins that have the full range of biological activity of human erythropoietin or only certain biological activities of erythropoietin. Improved therapeutic regimens where the erythropoietin is administered at concentrations below those required to stimulate hematopoiesis are also provided.

4 Claims, 25 Drawing Sheets

OTHER PUBLICATIONS

Juul et al. Erythropoietin and Erythropoietin Receptor in the Developing Human Central Nervous System, *Pedr. Res.* (1998) 43(1):40-49.

Juul et al., "Erythropoietin in the Cerebrospinal Fluid of Neonates who Sustained CNS Injury", *Ped. Res.* (1999) 46:(5):543-547.

Konishi et al., "Trophic Effect of Erythropoietin and Other Hematopoietic Factors on Central Cholinergic Neurons In Vitro and In Vivo", *Brain Res.* (1993) 609:29-35.

Koshimura et al., "Effects of Erythropoietin on Neuronal Activity", *J. Neurochem.* (1999) 72(6):2565-2572.

Sanford B. Krantz et al., "Erythropoietin", *Blood* 77(3): 419-434.

Marti et al., "Detection of Erythropoietin in Human Liquor: Intrinsic Erythropoietin Production in the Brain", *Kidney Int.* (1997) 51(2):416-418.

Masuda et al., "A Novel Site of Erythropoietin Production: Oxygen-Dependent Production in Cultured Rat Astrocytes", *J. Biol. Chem.* (1994) 269(30):19488-19493.

Mattson et al., "Calcium, Free Radical and Excitotoxic Neuronal Death in Primary Cell Culture", *Methods Cell Biol.* (1994) 46:187-216.

Morishita et al., "Erythropoietin Receptor is Expressed in Rat Hippocampal and Cerebral Cortical Neurons, and Erythropoietin Prevent In Vitro Glutamate-Induced Neuronal Death", *Neurosci.* (1997) 76(1):105-116.

Nakamura et al., "Elevated Levels of Erythropoietin in Cerbrospinal Fluid of Depressed Patients", *Amer. J. Med. Sci.* (1998) 315:199-201.

Sadamoto et al., "Erythropoietin Prevent Place Navigation Disability and Cortical Infarction in Rats with Permanent Occlusion of the Middle Cerebral Artery", *Biochem. Biophys.Res. Comm.* (1998) 253:26-32; Article No. RC989748.

Sakanaka et al., "*In Vivo* Evidence that Erythropoietin Protects Neurons from Ischemic Damage", *Proc. Natl. Acad. Sci.* (1998) 95:4635-4640.

Silva et al., "Erythropoietin Can Promote Erythroid Progenitor Survival by Repressing Apoptosis Through $Bcl_{XL}$ and Bcl-2", *Blood* (1996) 88(5):1576-1582.

Smith-Swintosky et al., "Protease-Activated Receptor 2 (PAR-2) is Present in the Rat Hippocampus and is Associated with Neurodegeneration", *J. Neurochem.*, (1997) 69:1890-1896.

Tabira et al., "Neurotrophic Effect of Hematopoietc Cytokines on Cholinergic and Other Neurons In Vitro", *Int. J. Dev. Neurosci.* (1995) 13(3/4):241-252.

Winerals et al., "Effect of Human Erythropoietin Derived From Recombinant DNA on the Anaemia of Patients Maintained by Chronic Haemodialysis", *Lancet* (1986) 2(8517):1175-1177.

European Search Report dated Mar. 22, 2005 for corresponding Appln. No. EP 01941562.

Examiner's first report for Australian Patent Appln. No. 2001274904 dated Jun. 15, 2005.

Eur. J. Pharmacology (2000) 392(1-2): 31-4, "In Vivo Evidence that Erythropoietin had a Neuroprotective Effect During Subarachnoid Hemorrhage", Buemi M, Grasso G, Corica F, Calapai G, Salpietro FM, Casucelli T. Sfacteria A Aloisi C, Alafaci Cm Sturiale A, Frisina N, Tomasell F, Mar. 24, 2000.

* cited by examiner

RAT CEREBRAL CORTICAL CULTURES EXPRESS EPO RECEPTOR

RAT HIPPOCAMPAL CULTURES EXPRESS EPO RECEPTOR

EPO RECEPTOR IS EXPRESSED ON PC12 AND SK-N-MC CELLS

EPO INDUCED GENE EXPRESSION IN PC12 CELLS

Erythropoietin regulates the expression of the BCL family members $Bcl_{XL}$ and Bak.

EPO PROTECTS RAT CEREBRAL CORTICAL CELLS FROM GLUTAMATE TOXICITY

Treatment (n=8)

t-test (one-tailed) comparison between treatments * p<0.01; ** p<0.001

EPO PROTECTS PC12 CELLS FROM GLUTAMATE-INDUCED CELL DEATH

Erythropoietin protects PC-12 cells from glutamate mediated cytotoxicity.

EPO PROTECTS PC12 CELLS FROM NGF WITHDRAWAL-INDUCED CELL DEATH

Erythropoietin protects PC-12 cells against death induced by NGF withdrawal.

EPO PROMOTES NEURITE OUTGROWTH IN RAT CEREBRAL CORTICAL CULTURES

One-way ANOVA comparison between groups p<0.0001;
Dunnett's multiple comparison test p>0.05, ns
unpaired t-test (one-way) *p<0.05; p<0.01, *p<0.001

EPO PROMOTES NEURITE OUTGROWTH IN RAT HIPPOCAMPAL CULTURES

One-way ANOVA comparison between treatment groups p<0.0001;
Dunnett's multiple comparison test *p<0.01;
unpaired t-test (one-tailed) ***p<0.001; + p<0.0001

EMP-1 PROMOTES NEURITE OUTGROWTH IN RAT CEREBRAL CORTICAL CULTURES

EMP-1 PROMOTES NEURITE OUTGROWTH IN RAT HIPPOCAMPAL CULTURES

EMP-6 PROMOTES NEURITE OUTGROWTH IN RAT CEREBRAL CORTICAL CULTURES

EMP-6 PROMOTES NEURITE OUTGROWTH IN RAT HIPPOCAMPAL CULTURES

EMP-9 PROMOTES NEURITE OUTGROWTH IN RAT CEREBRAL CORTICAL CULTURES

EMP-9 Concentration (n=16)

EMP-9 PROMOTES NEURITE OUTGROWTH IN RAT HIPPOCAMPAL CULTURES

EMP-23 PROMOTES NEURITE OUTGROWTH IN RAT CEREBRAL CORTICAL CULTURES

EMP-23 PROMOTES NEURITE OUTGROWTH IN RAT HIPPOCAMPAL CULTURES

EMP-27 PROMOTES NEURITE OUTGROWTH IN RAT CEREBRAL CORTICAL CULTURES

EMP-27 PROMOTES NEURITE OUTGROWTH IN RAT HIPPOCAMPAL CULTURES

STUDY I: EPO PROTECTS AGAINST ISCHEMIC INJURY BY CONTINUOUS INTRAVENOUS INFUSION VIA OSMOTIC MINI-PUMP

One-way ANOVA comparison between treatments p=0.01
t-test (one-tailed) comparison between treatments * p≤0.01

STUDY I: PLASMA DETERMINATIONS

STUDY II: EPO DOES NOT PROTECT AGAINST ISCHEMIC INJURY WHEN ADMINISTERED AS A SINGLE INTRAVENOUS BOLUS

One-way ANOVA comparison between treatment groups; p>0.05, n.s.

STUDY II: PLASMA DETERMINATIONS

STUDY III: EPO PROTECTS AGAINST ISCHEMIC INJURY VIA REPEAT INTRAVENOUS BOLUS DOSING

One-way ANOVA comparison between treatment groups p=0.02
Dunnett's multiple comparison t-test * p<0.05

STUDY III: PLASMA DETERMINATIONS

Study III: Plasma Concentration

SEQUENCE LISTING

<160> NUMBER OF SEQ ID NOS: 49

<210> SEQ ID NO 1
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa is Cys,Glu,Ala,a-amino gamma bromobutyric acid,homocysteine
<220> FEATURE:
<221> NAME/KEY: misc_feature
<222> LOCATION: (2)..(2)
<223> OTHER INFORMATION: Xaa is Arg,His,Tyr,Leu,Val
<220> FEATURE:
<221> NAME/KEY: misc_feature
<222> LOCATION: (3)..(3)
<223> OTHER INFORMATION: Xaa is Met,Phe,Ile
<220> FEATURE:
<221> NAME/KEY: misc_feature
<222> LOCATION: (6)..(6)
<223> OTHER INFORMATION: Xaa is any L or D amino acid
<220> FEATURE:
<221> NAME/KEY: misc_feature
<222> LOCATION: (9)..(9)
<223> OTHER INFORMATION: Xaa is Asp,Glu,Ile,Leu,Val
<220> FEATURE:
<221> NAME/KEY: misc_feature
<222> LOCATION: (10)..(10)
<223> OTHER INFORMATION: Xaa is Cys,Lys,Ala,alfa amino gamma bromobutyric acid,homocysteine

<400> SEQUENCE: 1

Xaa Xaa Xaa Gly Pro Xaa Thr Trp Xaa Xaa
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Xaa is any L or D amino acid
<220> FEATURE:
<221> NAME/KEY: misc_feature
<222> LOCATION: (3)..(3)
<223> OTHER INFORMATION: Xaa is Cys
<220> FEATURE:
<221> NAME/KEY: misc_feature
<222> LOCATION: (4)..(4)
<223> OTHER INFORMATION: Xaa is any any L or D amino acid
<220> FEATURE:
<221> NAME/KEY: misc_feature
<222> LOCATION: (5)..(5)
<223> OTHER INFORMATION: Xaa is any any L or D amino acid
<220> FEATURE:
<221> NAME/KEY: misc_feature
<222> LOCATION: (8)..(8)
<223> OTHER INFORMATION: Xaa is Cys
<220> FEATURE:
<221> NAME/KEY: misc_feature
<222> LOCATION: (11)..(11)
<223> OTHER INFORMATION: Xaa is any any L or D amino acid
<220> FEATURE:
<221> NAME/KEY: misc_feature
<222> LOCATION: (12)..(12)
<223> OTHER INFORMATION: Xaa is any any L or D amino acid

```
<400> SEQUENCE: 2

Tyr Xaa Xaa Xaa Xaa Gly Pro Xaa Thr Trp Xaa Xaa
1               5                   10

<210> SEQ ID NO 3
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa is any L or D amino acid
<220> FEATURE:
<221> NAME/KEY: misc_feature
<222> LOCATION: (3)..(3)
<223> OTHER INFORMATION: Xaa is any L or D amino acid
<220> FEATURE:
<221> NAME/KEY: misc_feature
<222> LOCATION: (4)..(4)
<223> OTHER INFORMATION: Xaa is Cys, Glu, Ala
<220> FEATURE:
<221> NAME/KEY: misc_feature
<222> LOCATION: (5)..(5)
<223> OTHER INFORMATION: Xaa is Arg, His, Tyr
<220> FEATURE:
<221> NAME/KEY: misc_feature
<222> LOCATION: (6)..(6)
<223> OTHER INFORMATION: Xaa is Met, Phe, Ile
<220> FEATURE:
<221> NAME/KEY: misc_feature
<222> LOCATION: (9)..(9)
<223> OTHER INFORMATION: Xaa is any L or D amino acid
<220> FEATURE:
<221> NAME/KEY: misc_feature
<222> LOCATION: (12)..(12)
<223> OTHER INFORMATION: Xaa is Cys, Lys, Ala
<220> FEATURE:
<221> NAME/KEY: misc_feature
<222> LOCATION: (13)..(13)
<223> OTHER INFORMATION: Xaa is any L or D amino acid
<220> FEATURE:
<221> NAME/KEY: misc_feature
<222> LOCATION: (14)..(14)
<223> OTHER INFORMATION: Xaa is any L or D amino acid
<220> FEATURE:
<221> NAME/KEY: misc_feature
<222> LOCATION: (15)..(15)
<223> OTHER INFORMATION: Xaa is any L or D amino acid
<220> FEATURE:
<221> NAME/KEY: misc_feature
<222> LOCATION: (16)..(16)
<223> OTHER INFORMATION: Xaa is any L or D amino acid

<400> SEQUENCE: 3

Xaa Tyr Xaa Xaa Xaa Xaa Gly Pro Xaa Thr Trp Xaa Xaa Xaa Xaa
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa is L or D amino acid
<220> FEATURE:
<221> NAME/KEY: misc_feature
<222> LOCATION: (3)..(3)
<223> OTHER INFORMATION: Xaa is L or D amino acid
<220> FEATURE:
<221> NAME/KEY: misc_feature
```

```
<222> LOCATION: (5)..(5)
<223> OTHER INFORMATION: Xaa is Arg, His, or Tyr
<220> FEATURE:
<221> NAME/KEY: misc_feature
<222> LOCATION: (6)..(6)
<223> OTHER INFORMATION: Xaa is Met, Phe, or lle
<220> FEATURE:
<221> NAME/KEY: misc_feature
<222> LOCATION: (9)..(9)
<223> OTHER INFORMATION: Xaa is L or D amino acid
<220> FEATURE:
<221> NAME/KEY: misc_feature
<222> LOCATION: (12)..(12)
<223> OTHER INFORMATION: Xaa is Cys, Lys, or Ala
<220> FEATURE:
<221> NAME/KEY: misc_feature
<222> LOCATION: (14)..(16)
<223> OTHER INFORMATION: Xaa is L or D amino acid

<400> SEQUENCE: 4

Xaa Tyr Xaa Cys Xaa Xaa Gly Pro Xaa Thr Trp Xaa Cys Xaa Xaa Xaa
 1               5                  10                  15

<210> SEQ ID NO 5
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa is any L or D amino acid
<220> FEATURE:
<221> NAME/KEY: misc_feature
<222> LOCATION: (3)..(3)
<223> OTHER INFORMATION: Xaa is L or D amino acid
<220> FEATURE:
<221> NAME/KEY: misc_feature
<222> LOCATION: (5)..(5)
<223> OTHER INFORMATION: Xaa is Arg, His
<220> FEATURE:
<221> NAME/KEY: misc_feature
<222> LOCATION: (6)..(6)
<223> OTHER INFORMATION: Xaa is Met, Phe
<220> FEATURE:
<221> NAME/KEY: misc_feature
<222> LOCATION: (9)..(9)
<223> OTHER INFORMATION: Xaa is lle, Leu, Thr, Met, Val
<220> FEATURE:
<221> NAME/KEY: misc_feature
<222> LOCATION: (12)..(12)
<223> OTHER INFORMATION: Xaa is Asp, Val
<220> FEATURE:
<221> NAME/KEY: misc_feature
<222> LOCATION: (14)..(14)
<223> OTHER INFORMATION: Xaa is Gly, Lys, Leu, Gln, Arg, Ser, Thr
<220> FEATURE:
<221> NAME/KEY: misc_feature
<222> LOCATION: (15)..(15)
<223> OTHER INFORMATION: Xaa is Ala, Gly, Pro, Arg, Tyr
<220> FEATURE:
<221> NAME/KEY: misc_feature
<222> LOCATION: (16)..(16)
<223> OTHER INFORMATION: Xaa is L or D amino acid

<400> SEQUENCE: 5

Xaa Tyr Xaa Cys Xaa Xaa Gly Pro Xaa Thr Trp Xaa Cys Xaa Xaa Xaa
 1               5                  10                  15

<210> SEQ ID NO 6
<211> LENGTH: 16
<212> TYPE: PRT
<213> ORGANISM: Artificial Sequence
<220> FEATURE:
```

```
<223> OTHER INFORMATION: Synthetic Peptide
<220> FEATURE:
<221> NAME/KEY: misc_feature
<222> LOCATION: (1)..(1)
<223> OTHER INFORMATION: Xaa is Asp, Glu, Leu, Asn, Ser, Thr, Val
<220> FEATURE:
<221> NAME/KEY: misc_feature
<222> LOCATION: (3)..(3)
<223> OTHER INFORMATION: Xaa is Ala, His, Lys, Leu, Met, Ser, Thr
<220> FEATURE:
<221> NAME/KEY: misc_feature
<222> LOCATION: (5)..(5)
<223> OTHER INFORMATION: Xaa is Arg, His
<220> FEATURE:
<221> NAME/KEY: misc_feature
<222> LOCATION: (6)..(6)
<223> OTHER INFORMATION: Xaa is any L or D amino acid
<220> FEATURE:
<221> NAME/KEY: misc_feature
<222> LOCATION: (9)..(9)
<223> OTHER INFORMATION: Xaa is any L or D amino acid
<220> FEATURE:
<221> NAME/KEY: misc_feature
<222> LOCATION: (12)..(12)
<223> OTHER INFORMATION: Xaa is any L or D amino acid
<220> FEATURE:
<221> NAME/KEY: misc_feature
<222> LOCATION: (14)..(14)
<223> OTHER INFORMATION: Xaa is Lys, Arg, Ser, Thr
<220> FEATURE:
<221> NAME/KEY: misc_feature
<222> LOCATION: (15)..(15)
<223> OTHER INFORMATION: Xaa is Pro
<220> FEATURE:
<221> NAME/KEY: misc_feature
<222> LOCATION: (16)..(16)
<223> OTHER INFORMATION: Xaa is any L or D amino acid

<400> SEQUENCE: 6

Xaa Tyr Xaa Cys Xaa Xaa Gly Pro Xaa Thr Trp Xaa Cys Xaa Xaa Xaa
1               5                   10                  15

<210> SEQ ID NO 7
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 7

Gly Gly Leu Tyr Leu Cys Arg Phe Gly Pro Val Thr Trp Asp Cys Gly
1               5                   10                  15

Tyr Lys Gly Gly
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 8

Gly Gly Thr Tyr Ser Cys His Phe Gly Pro Leu Thr Trp Val Cys Lys
1               5                   10                  15

Pro Gln Gly Gly
            20

<210> SEQ ID NO 9
<211> LENGTH: 20
<212> TYPE: PRT
```

```
<213> ORGANISM: Artificial Sequence
<220> FEATURE:
<223> OTHER INFORMATION: Synthetic Peptide

<400> SEQUENCE: 9

Gly Gly Asp Tyr His Cys Arg Met Gly Pro Leu Thr Trp Val Cys Lys
1               5                   10                  15

Pro Leu Gly Gly
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 10

Val Gly Asn Tyr Met Cys His Phe Gly Pro Ile Thr Trp Val Cys Arg
1               5                   10                  15

Pro Gly Gly Gly
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 11

Gly Gly Val Tyr Ala Cys Arg Met Gly Pro Ile Thr Trp Val Cys Ser
1               5                   10                  15

Pro Leu Gly Gly
            20

<210> SEQ ID NO 12
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 12

Val Gly Asn Tyr Met Ala His Met Gly Pro Ile Thr Trp Val Cys Arg
1               5                   10                  15

Pro Gly Gly

<210> SEQ ID NO 13
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 13

Gly Gly Thr Tyr Ser Cys His Phe Gly Pro Leu Thr Trp Val Cys Lys
1               5                   10                  15

Pro Gln

<210> SEQ ID NO 14
<211> LENGTH: 20
<212> TYPE: PRT
<213> ORGANISM: Artificial Sequence
```

```
<220> FEATURE:
<223> OTHER INFORMATION: Synthetic Peptide

<400> SEQUENCE: 14

Gly Gly Leu Tyr Ala Cys His Met Gly Pro Met Thr Trp Val Cys Gln
1               5                   10                  15

Pro Leu Arg Gly
            20

<210> SEQ ID NO 15
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 15

Thr Ile Ala Gln Tyr Ile Cys Tyr Met Gly Pro Glu Thr Trp Glu Cys
1               5                   10                  15

Arg Pro Ser Pro Lys Ala
            20

<210> SEQ ID NO 16
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 16

Tyr Ser Cys His Phe Gly Pro Leu Thr Trp Val Cys Lys
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 17

Tyr Cys His Phe Gly Pro Leu Thr Trp Val Cys
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 18

Ser Cys His Phe Gly Pro Leu Thr Trp Val Cys Lys
1               5                   10

<210> SEQ ID NO 19
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 19

Gly Gly Thr Ala Ser Cys His Phe Gly Pro Leu Thr Trp Val Cys Lys
1               5                   10                  15
```

```
Pro Gln Gly Gly
            20

<210> SEQ ID NO 20
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 20

Gly Gly Thr Tyr Ser Cys His Phe Ala Pro Leu Thr Trp Val Cys Lys
1               5                  10                  15

Pro Gln Gly Gly
            20

<210> SEQ ID NO 21
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 21

Gly Gly Thr Tyr Ser Cys Phe Gly Pro Leu Thr Trp Val Cys Lys Pro
1               5                  10                  15

Gln Gly Gly

<210> SEQ ID NO 22
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 22

Thr Tyr Ser Cys His Phe Gly Pro Leu Thr Trp Val Cys Lys Pro Gln
1               5                  10                  15

Gly Gly

<210> SEQ ID NO 23
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 23

Thr Tyr Ser Cys His Phe Gly Pro Leu Thr Trp Val Cys Lys Pro Gln
1               5                  10                  15

<210> SEQ ID NO 24
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 24

Tyr Ser Cys His Phe Gly Pro Leu Thr Trp Val Cys Lys Pro
1               5                  10

<210> SEQ ID NO 25
<211> LENGTH: 12
<212> TYPE: PRT
```

<213> ORGANISM: Artificial Sequence
<220> FEATURE:
<223> OTHER INFORMATION: Synthetic Peptide

<400> SEQUENCE: 25

Tyr Ser Cys His Phe Gly Pro Leu Thr Trp Val Cys
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 26

Tyr Ser Cys His Phe Gly Ala Leu Thr Trp Val Cys Lys
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 27

Gly Gly Cys Arg Ile Gly Pro Ile Thr Trp Val Cys Gly Gly
1               5                   10

<210> SEQ ID NO 28
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 28

His Phe Gly Pro Leu Thr Trp Val
1               5

<210> SEQ ID NO 29
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 29

Gly Gly Thr Thr Ser Cys His Phe Gly Pro Leu Thr Trp Val Cys Lys
1               5                   10                  15

Pro Gln Gly Gly
            20

<210> SEQ ID NO 30
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 30

Gly Gly Thr Phe Ser Cys His Phe Gly Pro Leu Thr Trp Val Cys Lys
1               5                   10                  15

Pro Gln Gly Gly
            20

<210> SEQ ID NO 31
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 31

Gly Gly Thr Tyr Ser Cys His Phe Gly Ala Leu Thr Trp Val Cys Lys
1               5                   10                  15

Pro Gln Gly Gly
            20

<210> SEQ ID NO 32
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 32

Gly Gly Thr Tyr Ser Cys His Phe Gly Pro Ala Thr Trp Val Cys Lys
1               5                   10                  15

Pro Gln Gly Gly
            20

<210> SEQ ID NO 33
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 33

Gly Gly Thr Tyr Ser Cys His Phe Gly Pro Leu Ala Trp Val Cys Lys
1               5                   10                  15

Pro Gln Gly Gly
            20

<210> SEQ ID NO 34
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 34

Gly Gly Thr Tyr Ser Cys His Phe Gly Pro Leu Thr Ala Val Cys Lys
1               5                   10                  15

Pro Gln Gly Gly
            20

<210> SEQ ID NO 35
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 35

Gly Gly Thr Tyr Ser Cys His Phe Gly Pro Leu Thr Phe Val Cys Lys
1               5                   10                  15

Pro Gln Gly Gly

```
<210> SEQ ID NO 36
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 36

Gly Gly Thr Tyr Ser Cys His Phe Gly Pro Leu Thr Trp Val Cys Lys
1               5                   10                  15

Ala Gln Gly Gly
            20

<210> SEQ ID NO 37
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (4)..(4)
<223> OTHER INFORMATION: Xaa is D-Tyr

<400> SEQUENCE: 37

Gly Gly Thr Xaa Ser Cys His Phe Gly Pro Leu Thr Trp Val Cys Lys
1               5                   10                  15

Pro Gln Gly Gly
            20

<210> SEQ ID NO 38
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (4)..(4)
<223> OTHER INFORMATION: Xaa is p-NO2-Phe

<400> SEQUENCE: 38

Gly Gly Thr Xaa Ser Cys His Phe Gly Pro Leu Thr Trp Val Cys Lys
1               5                   10                  15

Pro Gln Gly Gly
            20

<210> SEQ ID NO 39
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (4)..(4)
<223> OTHER INFORMATION: Xaa is p-NH2-Phe

<400> SEQUENCE: 39

Gly Gly Thr Xaa Ser Cys His Phe Gly Pro Leu Thr Trp Val Cys Lys
1               5                   10                  15

Pro Gln Gly Gly
            20
```

```
<210> SEQ ID NO 40
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (4)..(4)
<223> OTHER INFORMATION: Xaa is p-F-Phe

<400> SEQUENCE: 40

Gly Gly Thr Xaa Ser Cys His Phe Gly Pro Leu Thr Trp Val Cys Lys
1               5                   10                  15

Pro Gln Gly Gly
            20

<210> SEQ ID NO 41
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (4)..(4)
<223> OTHER INFORMATION: Xaa is p-I-Phe

<400> SEQUENCE: 41

Gly Gly Thr Xaa Ser Cys His Phe Gly Pro Leu Thr Trp Val Cys Lys
1               5                   10                  15

Pro Gln Gly Gly
            20

<210> SEQ ID NO 42
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (4)..(4)
<223> OTHER INFORMATION: Xaa is 3,5-dibromo-Tyr

<400> SEQUENCE: 42

Gly Gly Thr Xaa Ser Cys His Phe Gly Pro Leu Thr Trp Val Cys Lys
1               5                   10                  15

Pro Gln Gly Gly
            20

<210> SEQ ID NO 43
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa is Ac-Gly

<400> SEQUENCE: 43

Xaa Gly Thr Tyr Ser Cys His Phe Gly Pro Leu Thr Trp Val Cys Lys
1               5                   10                  15

Pro Gln Gly Gly
            20
```

```
<210> SEQ ID NO 44
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 44

Gly Gly Leu Tyr Ala Cys His Met Gly Pro Met Thr Trp Val Cys Gln
1               5                   10                  15

Pro Leu Gly Gly
            20

<210> SEQ ID NO 45
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 45

Leu Gly Arg Lys Tyr Ser Cys His Phe Gly Pro Leu Thr Trp Val Cys
1               5                   10                  15

Gln Pro Ala Lys Lys Asp
            20

<210> SEQ ID NO 46
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 46

Gly Gly Thr Tyr Ser Glu His Phe Gly Pro Leu Thr Trp Val Lys Lys
1               5                   10                  15

Pro Gln Gly Gly
            20

<210> SEQ ID NO 47
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa is Arg, His, Tyr, Leu, Trp
<220> FEATURE:
<221> NAME/KEY: misc_feature
<222> LOCATION: (2)..(2)
<223> OTHER INFORMATION: Xaa is Phe, Met, lle
<220> FEATURE:
<221> NAME/KEY: misc_feature
<222> LOCATION: (3)..(3)
<223> OTHER INFORMATION: Xaa is Gly, Ala
<220> FEATURE:
<221> NAME/KEY: misc_feature
<222> LOCATION: (4)..(4)
<223> OTHER INFORMATION: Xaa is Pro, Ala
<220> FEATURE:
<221> NAME/KEY: misc_feature
<222> LOCATION: (5)..(5)
<223> OTHER INFORMATION: Xaa is any L or D amino acid
<220> FEATURE:
<221> NAME/KEY: misc_feature
<222> LOCATION: (6)..(6)
<223> OTHER INFORMATION: Xaa is Thr, Ala
```

```
<220> FEATURE:
<221> NAME/KEY: misc_feature
<222> LOCATION: (7)..(7)
<223> OTHER INFORMATION: Xaa is Trp, Ala, Phe
<220> FEATURE:
<221> NAME/KEY: misc_feature
<222> LOCATION: (8)..(8)
<223> OTHER INFORMATION: Xaa is Asp, Val, Glu, lle, Leu

<400> SEQUENCE: 47

Xaa Xaa Xaa Xaa Xaa Xaa Xaa Xaa
1               5

<210> SEQ ID NO 48
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa is Arg, His, Tyr, Leu, Trp
<220> FEATURE:
<221> NAME/KEY: misc_feature
<222> LOCATION: (2)..(2)
<223> OTHER INFORMATION: Xaa is Phe, Met, lle
<220> FEATURE:
<221> NAME/KEY: misc_feature
<222> LOCATION: (5)..(5)
<223> OTHER INFORMATION: Xaa is any L or D amino Acid
<220> FEATURE:
<221> NAME/KEY: misc_feature
<222> LOCATION: (8)..(8)
<223> OTHER INFORMATION: xaa is Asp, Val, Glu, lle, Leu

<400> SEQUENCE: 48

Xaa Xaa Gly Pro Xaa Thr Trp Xaa
1               5

<210> SEQ ID NO 49
<211> LENGTH: 12
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Xaa is D-Tyr,p-NO2-Phe,p-NH2-Phe,p-F-Phe,
     p-I-Phe,3,5-dibromo-Tyr
<220> FEATURE:
<221> NAME/KEY: misc_feature
<222> LOCATION: (2)..(2)
<223> OTHER INFORMATION: Xaa is any L or D amino acid
<220> FEATURE:
<221> NAME/KEY: misc_feature
<222> LOCATION: (3)..(3)
<223> OTHER INFORMATION: Xaa is Cys,Glu,Ala, (-amino-(-bromobutyric
     acid, homocysteine
<220> FEATURE:
<221> NAME/KEY: misc_feature
<222> LOCATION: (4)..(4)
<223> OTHER INFORMATION: Xaa is Arg, His, Tyr, Leu, Trp
<220> FEATURE:
<221> NAME/KEY: misc_feature
<222> LOCATION: (5)..(5)
<223> OTHER INFORMATION: Xaa is Phe, Met, lle
<220> FEATURE:
<221> NAME/KEY: misc_feature
<222> LOCATION: (8)..(8)
<223> OTHER INFORMATION: Xaa is any L or D amino acid
<220> FEATURE:
<221> NAME/KEY: misc_feature
<222> LOCATION: (11)..(11)
```

-continued

```
<223> OTHER INFORMATION: Xaa is Asp, Glu, Val, Ile, Leu
<220> FEATURE:
<221> NAME/KEY: misc_feature
<222> LOCATION: (12)..(12)
<223> OTHER INFORMATION: Xaa is Cys,Lys,Ala,
      (-amino-(-bromobutyric acid, homocysteine

<400> SEQUENCE: 49

Xaa Xaa Xaa Xaa Xaa Gly Pro Xaa Thr Trp Xaa Xaa
1               5                   10
```

NEUROPROTECTIVE PEPTIDES

CROSS-REFERENCE TO RELATED APPLICATION

This application claims the benefit of U.S. Provisional Application Ser. No. 60/207,654, filed May 26, 2000.

FIELD OF THE INVENTION

The present invention is directed to methods of treating diseases and conditions involving the nervous system by administration of compositions having the therapeutic activity of human erythropoietin. These compositions include therapeutic agents such as peptides, peptide dimers, polypeptides, and proteins that have the full range of biological activity of human erythropoietin or only certain biological activities of erythropoietin. The present invention also provides improved therapeutic regimens wherein the therapeutic agent is administered at concentrations below those required to stimulate hematopoiesis.

BACKGROUND OF THE INVENTION

Erythropoietin (EPO) is a glycoprotein hormone produced by the kidney in response to tissue hypoxia that stimulates red blood cell production in the bone marrow. The gene for erythropoietin has been cloned and expressed in Chinese hamster ovary (CHO) cells as described in U.S. Pat. No. 4,703,008. Recombinant human erythropoietin (r-HuEPO or Epoetin alfa) has an amino acid sequence identical to that of human urinary erythropoietin, and the two are indistinguishable in chemical, physical and immunological tests. Recombinant human erythropoietin acts by increasing the number of cells capable of differentiating into mature erythrocytes, triggering their differentiation and augmenting hemoglobin synthesis in developing erythroblasts (Krantz S B. *Blood* (1991) 77: 419–434, Beckman B S, Mason-Garcia M. *The Faseb Journal* (1991) 5: 2958–2964).

Epoetin alfa has been well tolerated in studies conducted to date. Hypertensive encephalopathy and seizures have occasionally been described in dialysis patients treated with Epoetin alfa, particularly during the early phase of therapy when hematocrit is rising. (Eschbach J W, Egrie J C, Downing M R, Browne J K, Adamson J W. *New Engl J Med* (1987) 316: 73–78, Winearls C G, Oliver D O, Pippard M J, et al. *Lancet* (1986) 2 (8517): 1175–1177). Such reports became more rare as experience of use of the compound developed. Occasionally, cancer patients treated with Epoetin alfa have experienced an increase in blood pressure associated with a significant increase in hematocrit. The risk, however, appears substantially lower than in chronic renal failure patients.

No antibody titers against Epoetin alfa could be demonstrated and confirmed in subjects treated with Epoetin alfa for up to 2 years, indicating the absence of immunological sensitivity to Epoetin alfa. Skin rashes and urticaria have been observed rarely and when reported have been mild and transient in nature, but these events suggest allergic hypersensitivity to some components of the Epoetin alfa formulation.

Epoetin alfa is approved for sale in many countries for the treatment of anemia in chronic renal failure (dialysis and predialysis), anemia in zidovudine treated HIV positive patients (US), anemia in cancer patients receiving platinum-based chemotherapy, as a facilitator of autologous blood pre-donation, and as a peri-surgical adjuvant to reduce the likelihood of requiring allogeneic blood transfusions in patients undergoing orthopedic surgery.

EPO influences neuronal stem cells, likely during embryonic development, and possibly during in vitro experiments of differentiation. (Juul et al *Pediatr Dev Pathol* (1999) 2(2) 148–158. Juul et al *Pediatr Res* (1998) 43(1) 40–49.) Further, neonates and infants that suffer CNS injury via hypoxia, meningitis, and intraventricular hemorrhage, show an EPO induced neuroprotective effect (Juul et al *Ped Res* (1999) 46(5) 543–547.)

EPO helps prevent apoptosis of neural tissue in cases of injury that create hypoxia. This may be the result of EPO produced locally by astrocytes (Morishita et al *Neuroscience* (1996) 76(1) 105–116). Neuroprotection has been demonstrated in gerbil hippocampal and rat cerebrocortical tissue (Sakanaka et al *PNAS* (1998) 95(8) 4635–4640. Sadamoto et al *Biochem Biophys Res Commun* (1998) 253(1) 26–32).

EPO induces biological effects of PC12 cells, including changes in $Ca^{2+}$, changes in membrane potential, and promotion of neuronal survival. This has been interpreted that EPO can stimulate neural function and viability (Koshimura et al J. Neurochem (1999) 72(6) 2565–2572. Tabria et al *Int J Dev Neurosci* (1995) 13(3/4) 241–252.).

O'Brien et al propose that a 17 amino acid peptide sequence of EPO can act through the EPO-R (Erythropoietin receptor) to induce biological activity in NS20Y, SK-N-MC, and PC12 cells, which includes sprouting, differentiation and neuroprotection. Curiously this peptide does not promote proliferation of hematologic cells, thus it appears inactive in cell lines well understood for their sensitivity to EPO activity. (Campana et al *Int J Mol Med* (1998) 1(1) 235–241 and U.S. Pat. Nos. 5,700,909, issued on Dec. 23, 1999, 5,571,787, issued on Nov. 5, 1996, 5,714,459, issued on Feb. 3, 1998, and 5,696,080, issued on Dec. 9, 1997, all to O'Brien et al.)

EPO may influence neuronal stem cell commitment to drive differentiation of neurons as opposed to astrocytes or oligodendrocytes. This is compared to a similar activity of EPO, where it functions to drive commitment of hematopoietic stem cells to produce red blood cells (RBCs). There is an apparent relationship between CNS hypoxic injury, resulting in the production of EPO from astrocytes that commits neuronal stem cells to differentiate into neurons, while simultaneously acting as a neuroprotective function for existing neurons. (WIPO publication number WO99/21966, published on May 6, 1999, Weiss et al.)

SUMMARY OF THE INVENTION

The present invention is directed to methods of treating diseases and conditions involving the nervous system by administration of compositions having the neurological therapeutic activity of human erythropoietin.

In a first embodiment, the present invention is directed to a method for treating a patient having a disorder characterized by neurotoxicity, neurodegeneration or neurological damage, comprising administering to said patient a therapeutically effective amount of a peptide comprising one or more monomeric peptides of 8 to about 40 amino acids in length that bind to EPO receptor, each monomeric peptide comprising a sequence of amino acids $X_4X_5X_aX_bX_6X_cX_dX_7$ (SEQ ID NO: 47), wherein $X_a$ is G or A;
$X_b$ is P or A;
$X_c$ is T or A;
$X_d$ is selected from W, A, and F;

$X_4$ is selected from R, H, Y, L, and W, or $X_4$ is nonexistent;

$X_5$ is selected from F, M, and I;

$X_6$ is independently selected from the 20 genetically coded L-amino acids or the stereoisomeric D-amino acids; and $X_7$ is selected from D, V, E, I, and L.

In particular, said sequence is $X_3X_4X_5GPX_6TWX_7X_8$ (SEQ ID NO: 1), wherein $X_3$ is selected from C, E, A, α-amino-γ-bromobutyric acid, and homocysteine (Hoc); and $X_8$ is selected from C, K, A, α-amino-γ-bromobutyric acid, and homocysteine (Hoc).

In a second embodiment, the present invention is directed to peptides which behave as cell-surface receptor agonists and antagonists, as well as dimers and multimers of such peptides which exhibit binding and signal initiation of growth factor-type receptors. In one embodiment, the present invention provides peptides which behave as EPO agonists. These peptides may be dimers or multimers of such peptides, preferably 14 to about 20 residues in length, comprising a core amino acid sequence of $X_3X_4X_5GPX_6TWX_7X_8$ (SEQ ID NO: 1) wherein each amino acid is indicated by standard one letter abbreviation; $X_3$ can be C, E, A, α-amino-γ-bromobutyric acid, or Hoc, where Hoc is homocysteine; $X_4$ can be R, H, Y, L, or W, or $X_4$ is nonexistent; $X_5$ can be M, F, or I; $X_6$ is independently any one of the 20 genetically coded L-amino acids or the stereoisomeric D-amino acids; $X_7$ can be D, E, I, L, or V; and $X_8$ can be C, K, A, α-amino-γ-bromobutyric acid, or Hoc, where Hoc is homocysteine.

Preferably, the monomeric peptide unit of the dimer or multimer comprises a core sequence of amino acids $YX_2X_3X_4X_5GPX_6TWX_7X_8$ (SEQ ID NO: 2), wherein each of $X_2$ and $X_6$ is independently any one of the 20 genetically coded L-amino acids; $X_3$ is C; and $X_8$ is C.

Preferably, the monomeric peptide unit of the dimer comprises a core sequence of amino acids $X_1YX_2X_3X_4X_5GPX_6TWX_7X_8X_9X_{10}X_{11}$ (SEQ ID NO: 3), wherein each of $X_1$, $X_2$, $X_6$, $X_9$, $X_{10}$, and $X_{11}$, is independently selected from the 20 genetically coded L-amino acids. Particularly, $X_3$ can be C, E, A; $X_4$ can be R, H, or Y, or $X_4$ is nonexistent; $X_5$ can be M, F, or I; $X_7$ can be D or V; and $X_8$ can be C, K, or A.

In a more preferred embodiment, both $X_3$ and $X_8$ are C and thus, the monomeric peptide unit of the dimer comprises a core sequence of amino acids $X_1$ $YX_2$ $CX_4$ $X_5$ $GPX_6$ $TWX_7$ $CX_9$ $X_{10}$ $X_{11}$ (SEQ ID NO: 4). Particularly, the monomeric peptide unit comprises a core sequence of amino acids $X_1$ $YX_2$ $CX_4$ $X_5$ $GPX_6$ $TWX_7$ $CX_9$ $X_{10}$ $X_{11}$ (SEQ ID NO: 5), where $X_4$ can be R or H; $X_5$ can be F or M; $X_6$ can be I, L, T, M, or V; $X_7$ is D or V; $X_9$ can be G, K, L, Q, R, S, or T; and $X_{10}$ can be A, G, P, R, or Y. More particularly, the monomeric peptide unit of the dimer will comprise a core sequence of amino acids $X_1$ $YX_2$ $CX_4$ $X_5$ $GPX_6$ $TWX_7$ $CX_9$ $X_{10}$ $X_{11}$ (SEQ ID NO: 6), where $X_1$ can be D, E, L, N, S, T, or V; $X_2$ can be A, H, K, L, M, S, or T; $X_4$ is R or H; $X_9$ can be K, R, S, or T; and $X_{10}$ is P.

Preferably, the monomeric peptide unit of the dimer will comprise a core sequence of amino acids $X_1$ $YX_2$ $CX_4$ $X_5$ $GPX_6$ $TWX_7$ $CX_9$ $X_{10}$ $X_{11}$ (SEQ ID NO: 6), where $X_1$ can be D, E, L, N, S, T, or V; $X_2$ can be A, H, K, L, M, S, or T; $X_4$ is R or H; $X_9$ can be K, R, S, or T; and $X_{10}$ is P.

Particularly preferred monomeric peptide units of the dimers include:

```
GGLYLCRFGPVTWDCGYKGG;                          (SEQ ID NO:7)

GGTYSCHFGPLTWVCKPQGG;     (aka EMP-1)          (SEQ ID NO:8)

GGDYHCRMGPLTWVCKPLGG;                          (SEQ ID NO:9)

VGNYMCHFGPITWVCRPGGG;                          (SEQ ID NO:10)

GGVYACRMGPITWVCSPLGG;                          (SEQ ID NO:11)

VGNYMAHMGPITWVCRPGG;                           (SEQ ID NO:12)

GGTYSCHFGPLTWVCKPQ;       (aka EMP-16)         (SEQ ID NO:13)

GGLYACHMGPMTWVCQPLRG;     (aka EMP-36)         (SEQ ID NO:14)

TIAQYICYMGPETWECRPSPKA;   (aka EMP-38)         (SEQ ID NO:15)

YSCHFGPLTWVCK;            (aka EMP-20          (SEQ ID NO:16)

YCHFGPLTWVC;              (aka EMP-23)         (SEQ ID NO:17)

SCHFGPLTWVCK;             (aka EMP-24)         (SEQ ID NO:18)

GGTASCHFGPLTWVCKPQGG;     (aka EMP-6)          (SEQ ID NO:19)

GGTYSCHFAPLTWVCKPQGG;     (aka EMP-9)          (SEQ ID NO:20)

GGTYSCFGPLTWVCKPQGG;      (aka EMP-27)         (SEQ ID NO:21)

TYSCHFGPLTWVCKPQGG;       (aka EMP-17)         (SEQ ID NO:22)

TYSCHFGPLTWVCKLPQ;        (aka EMP-18)         (SEQ ID NO:23)

YSCHFGPLTWVCKP;           (aka EMP-19)         (SEQ ID NO:24)

YSCHFGPLTWVC;             (aka EMP-21)         (SEQ ID NO:25)
```

-continued

| | | |
|---|---|---|
| YSCHFGALTWVCK; | (aka EMP-22) | (SEQ ID NO:26) |
| GGCRIGPITWVCGG; | (aka EMP-25) | (SEQ ID NO:27) |
| HFGPLTWV; | (aka EMP-26) | (SEQ ID NO:28) |
| GGTTSCHFGPLTWVCKPQGG; | (aka EMP-7) | (SEQ ID NO:29) |
| GGTFSCHFGPLTWVCKPQGG; | (aka EMP-8) | (SEQ ID NO:30) |
| GGTYSCHFGALTWVCKPQGG; | (aka EMP-10) | (SEQ ID NO:31) |
| GGTYSCHFGPATWVCKPQGG; | (aka EMP-11) | (SEQ ID NO:32) |
| GGTYSCHFGPLAWVCKPQGG; | (aka EMP-12) | (SEQ ID NO:33) |
| GGTYSCHFGPLTAVCKPQGG; | (aka EMP-13) | (SEQ ID NO:34) |
| GGTYSCHFGPLTFVCKPQGG; | (aka EMP-14) | (SEQ ID NO:35) |
| GGTYSCHFGPLTWVCKAQGG; | (aka EMP-15) | (SEQ ID NO:36) |
| GGTXSCHFGPLTWVCKPQGG; | (aka EMP-28, X = D-Tyr) | (SEQ ID NO:37) |
| GGTXSCHFGPLTWVCKPQGG; | (aka EMP-29, X = p-NO$_2$-Phe) | (SEQ ID NO:38) |
| GGTXSCHFGPLTWVCKPQGG; | (aka EMP-30, X = p-NH$_2$-Phe) | (SEQ ID NO:39) |
| GGTXSCHFGPLTWVCKPQGG; | (aka EMP-31, X = p-F-Phe) | (SEQ ID NO:40) |
| GGTXSCHFGPLTWVCKPQGG; | (aka EMP-32, X = p-I-Phe) | (SEQ ID NO:41) |
| GGTXSCHFGPLTWVCKPQGG; | (aka EMP-33, X = 3,5-dibromo-Tyr) | (SEQ ID NO:42) |
| Ac-GGTYSCHFGPLTWVCKPQGG; | (aka EMP-34) | (SEQ ID NO:43) |
| GGLYACHMGPMTWVCQPLGG; | (aka EMP-35) | (SEQ ID NO:44) |
| LGRKYSCHFGPLTWVCQPAKKD; and | (aka EMP-37) | (SEQ ID NO:45) |
| GGTYSEHFGPLTWVKKPQGG. | (aka EMP-39) | (SEQ ID NO:46) |

Preferably, monomeric peptide units of the dimers include:

| | |
|---|---|
| GGTYSCHFGPLTWVCKPQGG; | (SEQ ID NO:8) (aka EMP-1) |
| GGTASCHFGPLTWVCKPQGG; | (SEQ ID NO:19) (aka EMP-6) |
| GGTYSCHFAPLTWVCKPQGG; and | (SEQ ID NO:20) (aka EMP-9) |
| YCHFGPLTWVC; | (SEQ ID NO:17) (aka EMP-23) |

In accordance with the present invention the monomeric units of the dimers can be the same or different.

In a preferred embodiment polyethylene glycol (PEG) may be employed as a linker to form the dimeric peptides of the present invention through a covalent bond.

In another embodiment, the present invention is directed to pharmaceutical compositions comprising at least one peptide of the invention and a pharmaceutical carrier to be used in a method of treating or preventing neurotoxicity.

In a further embodiment, the present invention provides a method for therapeutically treating a mammal having a disease or condition resulting from a neurotoxic or neuro-degenerative or neuro-damaging event by administration of at least one of the peptides of the present invention.

In a still further embodiment, a method for therapeutically treating a mammal having a neurotoxic, neuro-damaging or neurodegenerative condition which may be modulated by EPO by using at least one of the peptides of the present invention is provided.

DETAILED DESCRIPTION

Figure 1A:
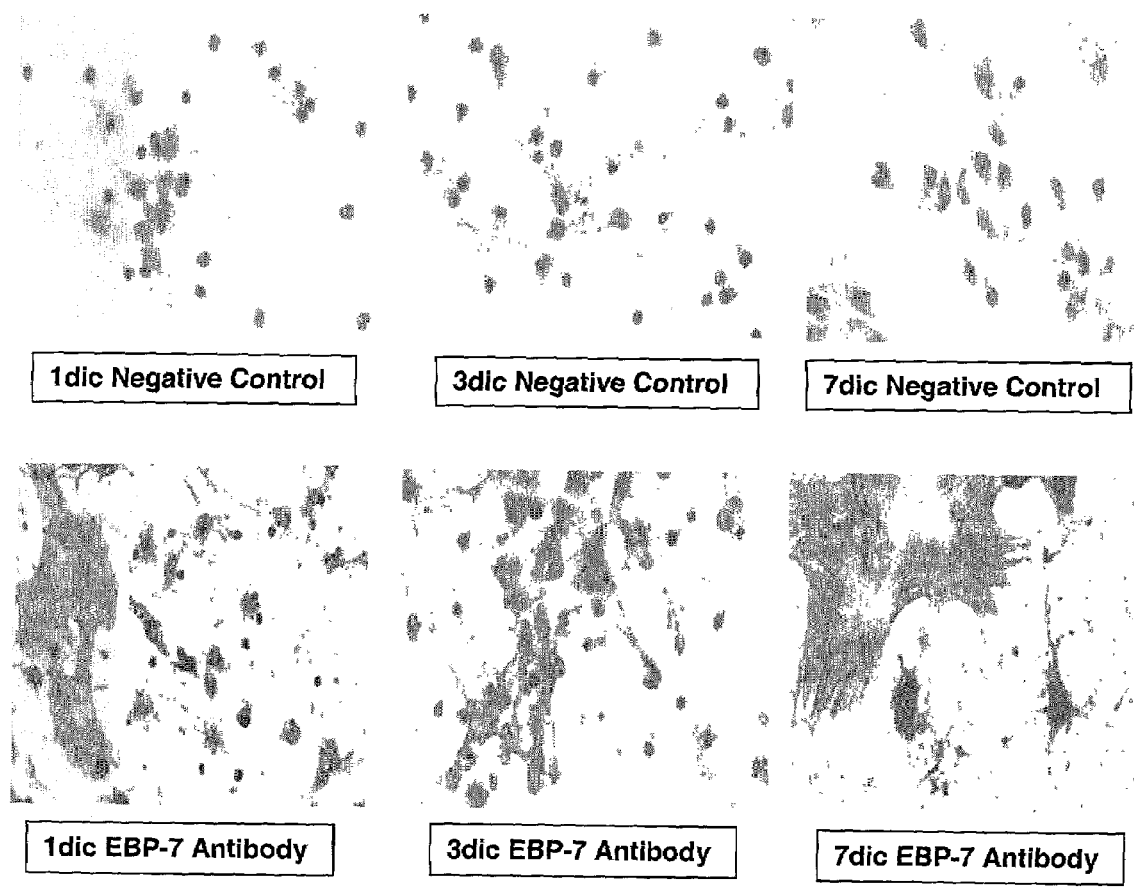
FIG. 1 Panel A and Panel B show that EPO receptor is expressed in rat hippocampal and cortical cultures.

"Erythropoietin" (EPO) used herein includes those peptides, peptide dimers, polypeptides, and proteins that have the full range of biological activity (for example, hematopoietic and neurological activities) of human erythropoietin or only certain biological activities (for example, hematopoietic or neurological activities only) of erythropoietin, as well as erythropoietin analogs, erythropoietin isoforms, erythropoietin mimetics, erythropoietin fragments, hybrid erythropoietin proteins, fusion proteins, oligomers and multimers of the above, homologues of the above, glycosylation pattern variants of the above, and muteins of the above, regardless of the biological activity of same, and further regardless of the method of synthesis or manufacture thereof including, but not limited to, recombinant, whether produced from cDNA or genomic DNA, synthetic, transgenic, and gene activated methods. Specific examples of erythropoietin include, Epoetin alfa (EPREX®, ERYPO®, PROCRIT®), NEORECORMON, Novel erythropoiesis stimulating protein (NESP or ARANESP, a hyperglycosylated analog of recombinant human erythropoietin (Epoetin) described in European patent application EP640619), human erythropoietin analog—human serum albumin fusion proteins such as those described in the international patent application WO 99/66054, erythropoietin mutants such as those described in the international patent application WO 99/38890, erythropoietin omega, which may be produced from an Apa I restriction fragment of the human erythropoietin gene described in U.S. Pat. No. 5,688,679, altered glycosylated human erythropoietin such as those described in the international patent application WO 99/11781, PEG conjugated erythropoietin analogs such as those described in WO 98/05363 or U.S. Pat. No. 5,643,575. Specific examples of cell lines modified for expression of endogenous human erythropoietin are described in international patent applications WO 99/05268 and WO 94/12650. The generally preferred form of EPO is purified, recombinant human EPO (rhEPO), currently formulated and distributed under the trademarks of EPREX®, ERYPO®, or PROCRIT®.

The abbreviation "EMP" as used herein refers to peptide mimetics of EPO, particularly certain peptides described in U.S. Pat. Nos. 5,767,078 and 5,773,569.

Following is a list of amino acid abbreviations used in the present specification for various peptides. The individual amino acid residues are identified according to a single letter and three letter code that is readily known and used by those of ordinary skill in the art.

| AMINO ACID | ABBREVIATIONS | |
|---|---|---|
| | 3-Letter | 1-Letter |
| alanine | ala | A |
| valine | val | V |
| leucine | leu | L |
| isoleucine | ile | I |
| proline | pro | P |
| phenylalanine | phe | F |
| tryptophan | trp | W |
| methionine | met | M |
| glycine | gly | G |
| serine | ser | S |
| threonine | thr | T |
| cysteine | cys | C |
| tyrosine | tyr | Y |
| asparagine | asn | N |
| glutamine | gln | Q |
| aspartic acid | asp | D |
| glutamic acid | glu | E |
| lysine | lys | K |
| arginine | arg | R |
| histidine | his | H |

In a first embodiment, the present invention is directed to methods of treating neuronal cells with a pharmaceutical composition comprising a therapeutically active peptide that behaves as cell-surface receptor agonists as well as dimers and multimers of such peptides that exhibit binding and signal initiation of growth factor-type receptors. In one embodiment, the present invention provides peptides that behave as EPO agonists. Particularly, these peptides may be dimers or multimers that have two 'monomeric' peptide units of 8 to 40 or more amino acids, preferably 14 to about 20 residues in length, comprising a core amino acid sequence of $X_3 X_4 X_5 GPX_6 TWX_7 X_8$ (SEQ ID NO: 1) where each amino acid is indicated by standard one letter abbreviation; $X_3$ can be C, E, A, α-amino-γ-bromobutyric acid, or Hoc, where Hoc is homocysteine; $X_4$ can be R, H, Y, L, or W, or $X_4$ is nonexistent; $X_5$ can be M, F, or I; $X_6$ is independently any one of the 20 genetically coded L-amino acids or the stereoisomeric D-amino acids; $X_7$ can be D, E, I, L, or V; and $X_8$ can be C, K, A, α-amino-γ-bromobutyric acid, or Hoc, where Hoc is homocysteine, provided that either $X_3$ or $X_8$ is C or Hoc. Preferably, the monomeric peptide unit of the dimer or multimer comprises a core sequence $YX_2X_3X_4X_5GPX_6TWX_7X_8$ (SEQ ID NO: 2) where each amino acid is indicated by standard one letter abbreviation; each $X_1, X_2, X_6, X_9, X_{10}$, and $X_{11}$ is independently selected from the 20 genetically coded L-amino acids; $X_3$ can be C, E, A, α-amino-γ-bromobutyric acid, or Hoc, where Hoc is homocysteine; $X_4$ can be R, H, Y, L, or W, or $X_4$ is nonexistent; $X_5$ can be M, F, or I; $X_7$ can be D, E, I, L, or V; and $X_8$ can be C, K, A, α-amino-γ-bromobutyric acid, or Hoc, where Hoc is homocysteine. More preferably, either $X_3$ or $X_8$ is C or Hoc.

Preferably, the monomeric peptide unit of the dimer or multimer comprises a core sequence of amino acids $YX_2X_3X_4X_5GPX_6TWX_7X_8$ (SEQ ID NO: 2), wherein each of $X_2$ and $X_6$ is independently any one of the 20 genetically coded L-amino acids; $X_3$ is C; and $X_2$ is C.

Preferably, the monomeric peptide unit of the dimer comprises a core sequence of amino acids $X_1YX_2X_3X_4X_5GPX_6TWX_7X_8X_9X_{10}X_{11}$ (SEQ ID NO: 3), wherein each of $X_1, X_2, X_6, X_9, X_{10}$, and $X_{11}$ is independently selected from the 20 genetically coded L-amino acids. Particularly, $X_3$ can be C, E, A; $X_4$ can be R, H, or Y, or $X_4$ is nonexistent; $X_5$ can be M, F, or I; $X_7$ can be D or V; and $X_8$ can be C, K, or A.

In a more preferred embodiment, both $X_3$ and $X_8$ are C and thus, the monomeric peptide unit of the dimer comprises a core sequence of amino acids $X_1 YX_2 CX_4 X_5 GPX_6 TWX_7 CX_9 X_{10} X_{11}$ (SEQ ID NO: 4). Particularly, the monomeric peptide unit comprises a core sequence of amino acids $X_1 YX_2 CX_4 X_5 GPX_6 TWX_7 CX_9 X_{10} X_{11}$ (SEQ ID NO: 5), where $X_4$ can be R or H; $X_5$ can be F or M; $X_6$ can be I, L, T, M, or V; $X_7$ is D or V; $X_9$ can be G, K, L, Q, R, S, or T; and $X_{10}$ can be A, G, P, R, or Y. More particularly, the monomeric peptide unit of the dimer will comprise a core sequence of amino acids $X_1 YX_2 CX_4 X_5 GPX_6 TWX_7 CX_9 X_{10} X_{11}$ (SEQ ID NO: 6), where $X_1$ can be D, E, L, N, S, T, or V; $X_2$ can be A, H, K, L, M, S, or T; $X_4$ is R or H; $X_9$ can be K, R, S, or T; and $X_{10}$ is P.

Preferably, the monomeric peptide unit of the dimer will comprise a core sequence of amino acids $X_1 YX_2 CX_4 X_5 GPX_6 TWX_7 CX_9 X_{10} X_{11}$ (SEQ ID NO: 6), where $X_1$ can be D, E, L, N, S, T, or V; $X_2$ can be A, H, K, L, M, S, or T; $X_4$ is R or H; $X_9$ can be K, R, S, or T; and $X_{10}$ is P.

Particularly preferred monomeric peptide units of the dimers include:

| | | |
|---|---|---|
| GGLYLCRFGPVTWDCGYKGG; | | (SEQ ID NO:7) |
| GGTYSCHFGPLTWVCKPQGG; | (aka EMP-1) | (SEQ ID NO:8) |
| GGDYHCRMGPLTWVCKPLGG; | | (SEQ ID NO:9) |
| VGNYMCHFGPITWVCRPGGG; | | (SEQ ID NO:10) |
| GGVYACRMGPITWVCSPLGG; | | (SEQ ID NO:11) |
| VGNYMAHMGPITWVCRPGG; | | (SEQ ID NO:12) |
| GGTYSCHFGPLTWVCKPQ; | (aka EMP-16) | (SEQ ID NO:13) |
| GGLYACHMGPMTWVCQPLRG; | (aka EMP-36) | (SEQ ID NO:14) |
| TIAQYICYMGPETWECRPSPKA; | (aka EMP-38) | (SEQ ID NO:15) |
| YSCHFGPLTWVCK; | (aka EMP-20) | (SEQ ID NO:16) |
| YCHFGPLTWVC; | (aka EMP-23) | (SEQ ID NO:17) |
| SCHFGPLTWVCK; | (aka EMP-24) | (SEQ ID NO:18) |
| GGTASCHFGPLTWVCKPQGG; | (aka EMP-6) | (SEQ ID NO:19) |
| GGTYSCHFAPLTWVCKPQGG; | (aka EMP-9) | (SEQ ID NO:20) |
| GGTYSCFGPLTWVCKPQGG; | (aka EMP-27) | (SEQ ID NO:21) |
| TYSCHFGPLTWVCKPQGG; | (aka EMP-17) | (SEQ ID NO:22) |
| TYSCHFGPLTWVCKPQ; | (aka EMP-18) | (SEQ ID NO:23) |
| YSCHFGPLTWVCKP; | (aka EMP-19) | (SEQ ID NO:24) |
| YSCHFGPLTWVC; | (aka EMP-21) | (SEQ ID NO:25) |
| YSCHFGALTWVCK; | (aka EMP-22) | (SEQ ID NO:26) |
| GGCRIGPITWVCGG; | (aka EMP-25) | (SEQ ID NO:27) |

-continued

| | | |
|---|---|---|
| HFGPLTWV; | (aka EMP-26) | (SEQ ID NO:28) |
| GGTTSCHFGPLTWVCKPQGG; | (aka EMP-7) | (SEQ ID NO:29) |
| GGTFSCHFGPLTWVCKPQGG; | (aka EMP-8) | (SEQ ID NO:30) |
| GGTYSCHFGALTWVCKPQGG; | (aka EMP-10) | (SEQ ID NO:31) |
| GGTYSCHFGPATWVCKPQGG; | (aka EMP-11) | (SEQ ID NO:32) |
| GGTYSCHFGPLAWVCKPQGG; | (aka EMP-12) | (SEQ ID NO:33) |
| GGTYSCHFGPLTAVCKPQGG; | (aka EMP-13) | (SEQ ID NO:34) |
| GGTYSCHFGPLTFVCKPQGG; | (aka EMP-14) | (SEQ ID NO:35) |
| GGTYSCHFGPLTWVCKAQGG; | (aka EMP-15) | (SEQ ID NO:36) |
| GGTXSCHFGPLTWVCKPQGG; | (aka EMP-28, X = D-Tyr) | (SEQ ID NO:37) |
| GGTXSCHFGPLTWVCKPQGG; | (aka EMP-29, X = p-NO$_2$-Phe) | (SEQ ID NO:38) |
| GGTXSCHFGPLTWVCKPQGG; | (aka EMP-30, X = p-NH$_2$-Phe) | (SEQ ID NO:39) |
| GGTXSCHFGPLTWVCKPQGG; | (aka EMP-31, X = p-F-Phe) | (SEQ ID NO:40) |
| GGTXSCHFGPLTWVCKPQGG; | (aka EMP-32, X = p-I-Phe) | (SEQ ID NO:41) |
| GGTXSCHFGPLTWVCKPQGG; | (aka EMP-33, X = 3,5-dibromo-Tyr) | (SEQ ID NO:42) |
| Ac-GGTYSCHFGPLTWVCKPQGG; | (aka EMP-34) | (SEQ ID NO:43) |
| GGLYACHMGPMTWVCQPLGG; | (aka EMP-35) | (SEQ ID NO:44) |
| LGRKYSCHFGPLTWVCQPAKKD; and | (aka EMP-37) | (SEQ ID NO:45) |
| GGTYSEHFGPLTWVKKPQGG. | (aka EMP-39) | (SEQ ID NO:46) |

Most preferably, monomeric peptide units of the dimers include:

| | |
|---|---|
| GGTYSCHFGPLTWVCKPQGG; | (SEQ ID NO:8) (aka EMP-1) |
| GGTASCHFGPLTWVCKPQGG; | (SEQ ID NO:19) (aka EMP-6) |
| GGTYSCHFAPLTWVCKPQGG; and | (SEQ ID NO:20) (aka EMP-9) |
| YCHFGPLTWVC. | (SEQ ID NO:17) (aka EMP-23) |

EPO is administered by any suitable means as appropriate for the particular patient being treated, as would be apparent to one skilled in the art. The phrase "therapeutically effective" as used herein will vary from patient-to-patient, and depending on the particular range of biological activities possessed by the EPO molecule being administered. Typically, for EPO having hematopoietic activity, a therapeutically effective amount will be from about 1 to 500 I.U./kg body weight and more preferably from 50 to 300 I.U./kg body weight especially when erythropoietin is administered via subcutaneously. For EPO molecules not possessing hematopoietic activity the therapeutically effective dose may be more or less that an EPO molecule having hematopoietic activity. The preferred methods of administration are intravenous (iv) and subcutaneous (sc), with subcutaneous being generally preferred. Hematopoietically active EPO is administered within the range of about 50–1000 U/kg per dose, one to five times per week. In another embodiment, the EPO composition is administered directly to the nervous system. This administration route includes, but is not limited to, the intracerebral, intraventricular, intracerebroventricular, intrathecal, intracisternal, intraspinal and/or peri-spinal routes of administration, which can employ intracranial and intravertebral needles, and catheters with or without pump devices. Infusion doses can range, for example, from about 1.0 to 50,000 U/kg/min of EPO composition over a period ranging from several minutes to several days. Hematopoietically active EPO administration is delayed or withheld if the patient, male or female, exhibits a hemoglobin level in excess of about 15 g/dL.

The present invention provides in one embodiment a method to treat acute and chronic neurodegenerative disorders comprising administration of EPO or analogs thereof. Acute neurodegenerative disorders include, but are not limited to, various types of acute neurodegenerative disorders associated with neuronal cell death or compromise including cerebrovascular insufficiency, focal or diffuse brain trauma, diffuse brain damage, and spinal cord injury. Examples of acute neurodegenerative disorders are: cerebral ischemia or infarction including embolic occlusion and thrombotic occlusion, reperfusion following acute ischemia, perinatal hypoxic-ischemic injury, cardiac arrest, as well as intracranial hemorrhage of any type (such as epidural, subdural, subarachnoid and intracerebral), and intracranial and intravertebral lesions (such as contusion, penetration, shear, compression and laceration), and whiplash shaken infant syndrome. Chronic neurodegenerative disorders that can be treated with one or more methods of the present invention include, but are not limited to, Alzheimer's disease, Pick's disease, diffuse Lewy body disease, progressive supranuclear palsy (Steel-Richardson syndrome), multisystem degeneration (Shy-Drager syndrome), chronic epileptic conditions associated with neurodegeneration, motor neuron diseases including amyotrophic lateral sclerosis, degenerative ataxias, cortical basal degeneration, ALS—Parkinson's—Dementia complex of Guam, subacute sclerosing panencephalitis, Huntington's disease, Parkinson's disease, synucleinopathies (including multiple system atrophy), primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, familial dysautonomia (Riley-Day syndrome), and prion diseases (including, but not limited to Creutzfeldt-Jakob, Gerstmann-Sträussler-Scheinker disease, Kuru and fatal familial insomnia).

Because of the combination of neuroprotection and neurite outgrowth induced by rhEPO, other clinical conditions can be treated with one or more methods of the present invention include treating and/or preventing the neurological (including, but not limited to, cognitive) and psychiatric (including, but not limited to, psychopathology, depression, or anxiety), manifestations associated with peripheral diseases including, but not limited to, EPO deficiency (e.g., renal disease), blood loss of any kind (including, but not limited to, hemodialysis, peritoneal dialysis, diagnostic sampling, occult gastrointestinal bleeding), renal failure and end-stage renal disease, renal transplantation, and other conditions associated with anemia and neurological and neuropsychiatric manifestations, including, but not limited to, hematological and non-hematological malignancies/cancer, symptoms or complications in patients receiving chemotherapy (including, but not limited to, cisplatin) and other drugs (including, but not limited to, zidovudine), other hematological disorders (including, but not limited to, sickle cell anemia and thalassemia), inflammatory and infectious disorders (including, but not limited to, human immunodeficiency viral infections), chronic systemic autoimmune diseases (including, but not limited to, systemic lupus erythematosus), Henoch Schonlein Purpura, and hemolytic uremic syndrome. Also included in the present invention are the treatment and/or prevention of neurological and neuropsychiatric manifestations resulting from chemical, toxic, infectious and radiation injury of the nervous system and as a result of prematurity, as well as the treatment and/or prevention of neurological and neuropsychiatric consequences of encephalopathies including, but not limited to, those of anoxic-ischemia, hepatic, glycemic, uremic, electrolyte and endocrine origin.

Also, because of the combination of neuroprotection and neurite outgrowth induced by rhEPO, this molecule can also be applicable for the treatment and/or prevention of plexopathies (including plexus palsies), multifocal neuropathies, sensory neuropathies, motor neuropathies, sensory-motor neuropathies, infections neuropathies, autonomic neuropathies, sensory-autonomic neuropathies, demyelinating neuropathies (including, but not limited to, Guillain-Barre syndrome and chronic inflammatory demyelinating polyradiculoneuropathy), other inflammatory and immune neuropathies, neuropathies induced by drugs, neuropathies induced by pharmacological treatments, neuropathies induced by toxins, traumatic neuropathies (including, but not limited to, compression, crush, laceration and segmentation neuropathies), metabolic neuropathies, endocrine and paraneoplastic neuropathies, and other neuropathies such as Charcot-Marie-Tooth disease (type 1a, 1b, 2, 4a, 1-X linked), Friedreich's ataxia, metachromatic leukodystrophy, Refsum's disease, adrenomyeloneuropathy, Ataxia-telangiectasia, Déjerine-Sottas neuropathy (types A and B), Lambert-Eaton syndrome, and disorders of the cranial nerves.

The following examples illustrate the present invention without, however, limiting the same thereto.

EXAMPLE 1 rhEPO is Expressed in Primary Rat Neuronal Cultures and in Neuronal Cell Lines

Primary Neuronal Cell Culture

Dissociated hippocampal and cortical cell cultures were established from embryonic day 18 rat fetuses as previously described (Mattson et al., 1994). Briefly, fetuses were removed via cesarean section from pregnant moms (Sprague-Dawley) anesthetized with halothane according to the AVMA Panel on Euthanasia. Pups were decapitated and the brains were removed and placed in HEPES-buffered Hank's Balanced Salt solution (HBSS; Gibco). The hippocampi and cortices were dissected out and pooled according to tissue-type. Tissue was trypsinized for 15 min (1 mg/ml trypsin-HBSS; Worthington), rinsed with fresh HBSS, incubated in trypsin inhibitor (1 mg/ml; Sigma) for 5 min, rinsed again with fresh HBSS and then triturated in 1 ml fresh HBSS with a fire-polished glass pipette. Dissociated cells were seeded at 30,000 cells/well onto poly-D-lysine coated 96-well plates (Collaborative BioScience). Each well contained 100 µl of Eagle's Minimal Essential Media (MEM; Gibco) supplemented with 26 mM $NaHCO_3$ (Sigma), 56 mM glucose (Sigma), 15 mM KCl (Sigma), 1 mM sodium pyruvate (Sigma), 1.1 mM L-glutamine (Sigma), 10% (v/v) heat-inactivated fetal bovine serum (Hyclone), and 0.001% gentamicin sulfate (Sigma) (pH 7.4). Cells were allowed to attach for 24 h in a humidified 37° C. 5% $CO_2$ incubator before experimental treatment. The culture media was aspirated and exchanged with fresh media every three days.

Immunocytochemistry

Parallel hippocampal and cortical cultures were treated as described above and were processed for immunocytochemistry (ICC) as described previously (Smith-Swintosky et al., 1997). Briefly, cells were plated onto four-chamber poly-D-lysine coated glass slides (LabTek, Napersville, Ill.). On the seventh day in culture, the culture media was removed and the cells were washed once with Dulbecco's phosphate buffered saline (DPBS; Sigma) and then fixed with 10% phosphate-buffered formalin for 15 min at room temperature. After fixation, the cultures were rinsed with DPBS and placed in blocking serum for 10 min (normal horse serum; 1:50 dilution in DPBS; Vector Labs, Burlingame, Calif.). Cultures were rinsed again and then incubated for 30 min in an anti-mouse monoclonal antibody specific to the EPO receptor (EBP-7); 1:75 dilution in antibody diluent (Zymed, South San Francisco, Calif.). Cultures were rinsed several times with DPBS, then exposed to biotinylated secondary antibody for 30 min (Vector Labs). Cultures were rinsed a final time and then incubated for 30 min in avidin-biotinylated horseradish peroxidase complex (mouse IgG ABC kit, Vector Labs). The presence of the primary antibody was detected using 3'3-diaminobenzidine tetrahydrochloride (DAB, Biomeda, Foster City, Calif.)—two exposures for 5 min each. Cells were then counterstained with hematoxylin, dehydrated, cleared, coverslipped and photographed under an Olympus BX-2 light microscope.

Results

Figure 1B:
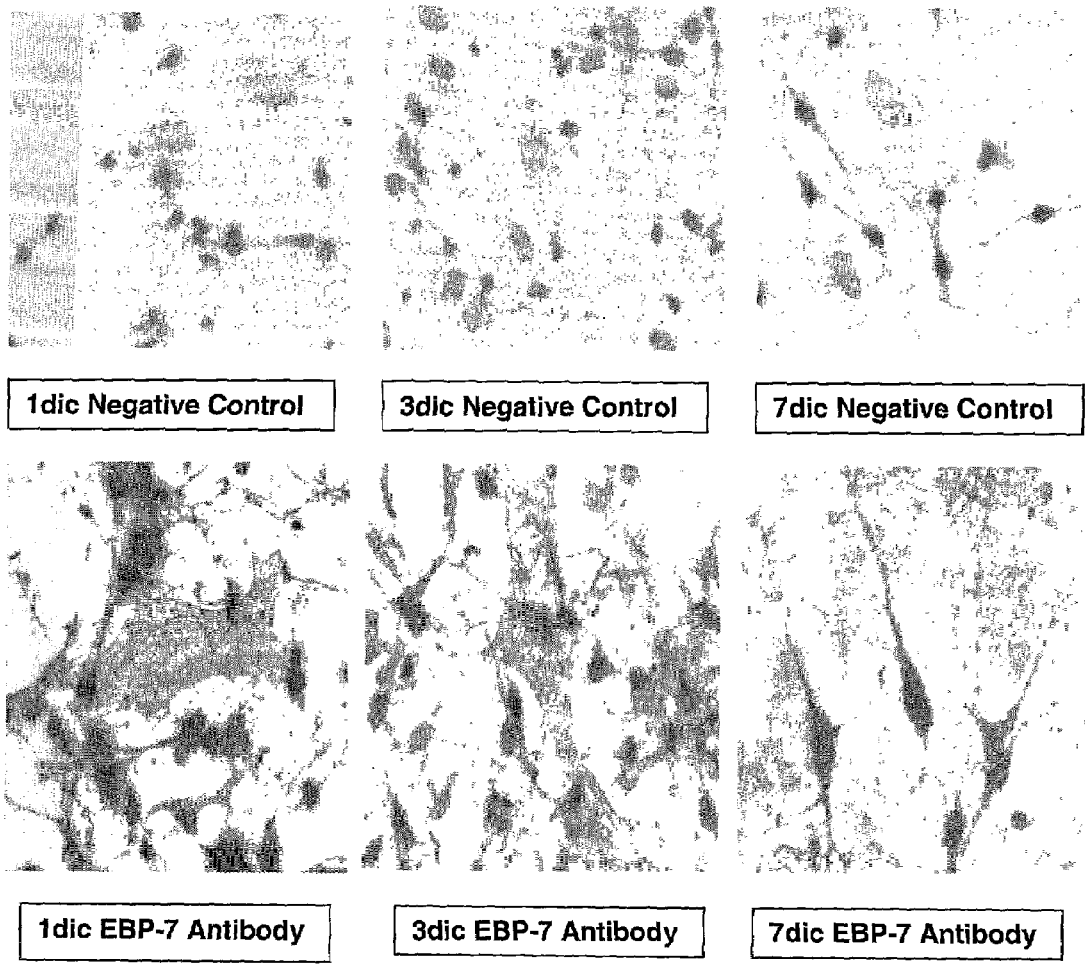

Robust staining for EPO receptor was observed in both neurons and glia within hippocampal and cortical cultures (FIG. 1a and FIG. 1b). EPO receptor expression levels appear to increase with time in culture.

Discussion

These results show that EPO plays a role in early development of the nervous system, particularly the hippocampus and cerebral cortex.

Immunohistochemistry of Neuronal Cell Lines

The neuronal cell lines PC-12, derived from a pheochromocytoma of the rat adrenal gland (Greene and Tischler, 1976), and SK-N-MC, obtained from a neuroepithelioma of a brain of human origin (Spengler et al., 1973), were used. PC-12 cells can be reversibly induced to the neuronal phenotype in the presence of nerve growth factor (NGF). PC-12 cells were grown on poly-D-Lysine coated tissue culture dishes in DMEM containing 10% horse serum and 5% FBS and in the presence of 0.1 µg/ml NGF for 7 days to induce the neuronal phenotype. SK-N-MC cells were cultured in minimal essential media supplemented with 1.0 mM Sodium pyruvate, 1.5 g/L sodium bicarbonate, 2 mM glutamine and 10% FBS for 4 days. PC-12 and SK-N-MC cells were cultured in a 96 well plate from Greiner, conducive for microscopy. On the day of the experiment cells were fixed in 10% Formalin containing 10% sucrose and incubated in blocking buffer (40 mM Tris HCL, Ph 8.0, 27 mM NaCl, and 0.2% Tween 20). Receptors for erythropoietin were detected by incubating the cells with a rabbit polyclonal, anti-erytbropoietin receptor antibody (C-20 from Santa Cruz) and a FITC conjugated secondary antibody. Labeled cells were visualized using a fluorescent microscope (ATTO).

Results

Figure 2:
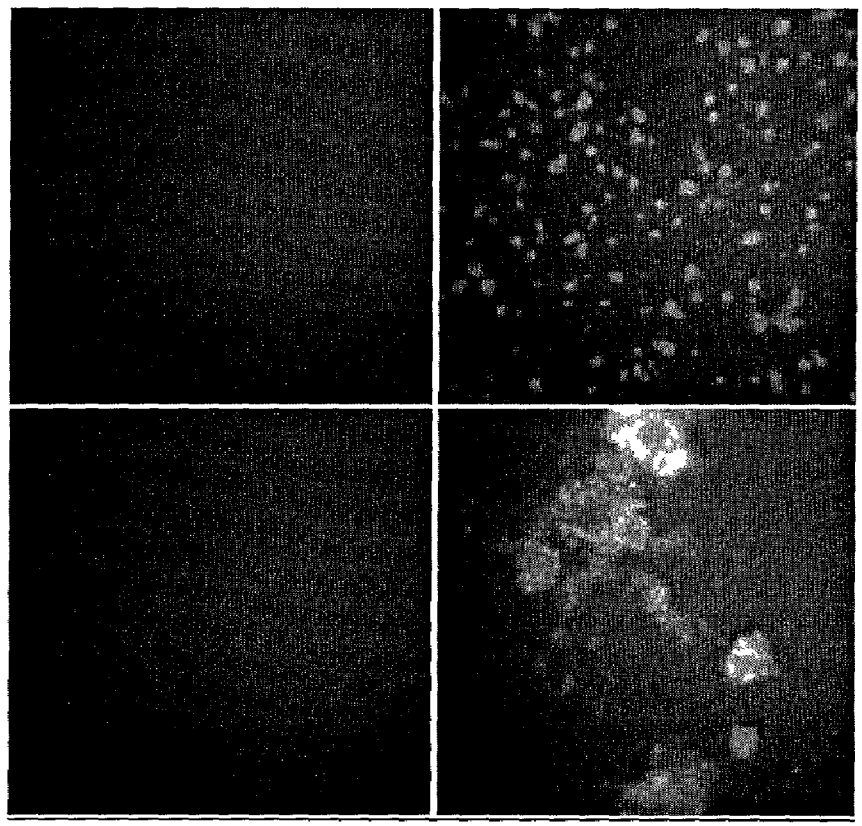
FIG. 2 shows that EPO receptor is expressed in neuronal cell lines: PC12 and SK-N-MC cells.

A polyclonal antibody against the erythropoietin receptor labeled both SK-N-MC and PC-12 cells as seen in FIG. 2 (right panels). All SK-N-MC cells visible at low magnification appeared to be labeled with the antibody. The majority of PC-12 cells that were detectable were labeled with the anti-erythropoietin receptor antibody. A few intact PC-12 cells that retained a characteristic neuronal phenotype in this preparation showed staining throughout the axonal process as well as in the cell body. Secondary antibody alone did not label either cell type (FIG. 2, left panels).

Therefore, these results demonstrate that these cell lines, SK-N-MC cells from a human neuroepithelioma and PC-12 cells from a rat pheochromocytoma, express the erythropoietin receptor. These cell lines are therefore responsive to erythropoietin and can provide a good system to study the effects of erythropoietin on neurons.

EXAMPLE 2

EPO Induced Gene Expression in PC12 Cells

Cell Culture

PC-12 cells (from a rat Pheochromocytoma) were cultured on poly-D-Lysine coated tissue culture plastic in DMEM containing 10% FBS and 5% Horse serum. To induce the neuronal phenotype in PC-12 cells, serum was removed and the cells were treated with NGF (50 ng/ml). Cells were grown for 7 days in the presence of the NGF then used for experiments.

EPO Treatment and RNA Isolation

PC-12 cells were cultured as described in Example 1 in a 10 cm poly-D-lysine coated tissue culture dish. Cells were incubated in the presence of 1 U/ml of EPO for 24 hr. Total RNAn was then isolated using a Qiagen RNAeasy mini prep kit and used for RT-PCR.

Quantitative RT-PCR

Real time reverse transcription and PCR were performed in a single reaction using a light cycler and an RNA amplification kit from Roche Molecular Biochemicals. RNA was quantitated and added in equal amounts to reaction mix that includes the dsDNA specific dye SYBR green I. Specific PCR reaction products are quantitated by detecting the amount of fluorescence in the reaction at each PCR cycle. Final analysis was performed using the data analysis software included with the light cycler instrument.

Summary

Figure 3:
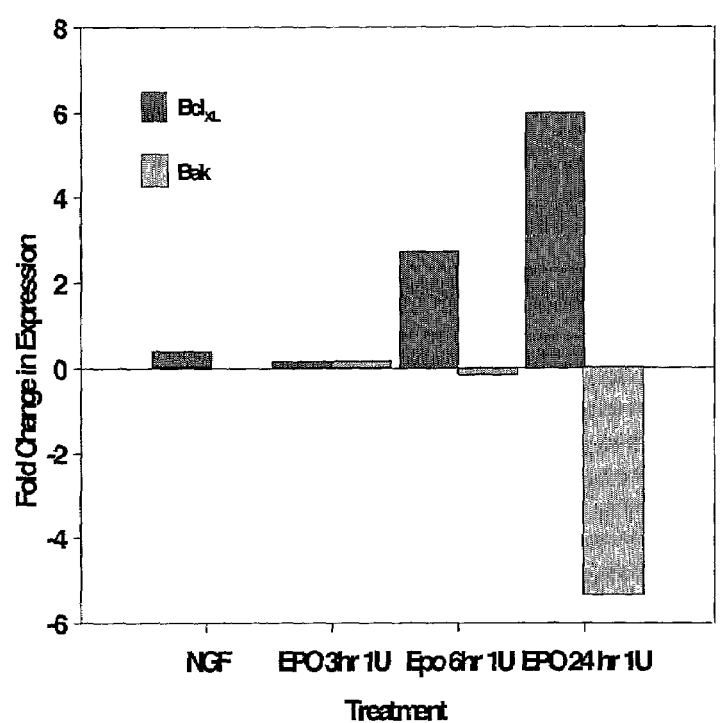
FIG. 3 shows EPO induced gene expression in PC12 cells. (Top) Total RNA isolated from PC-12 cells treated with 1 nm EPO for 24 hr was subject to RT-PCR to quantify the changes in gene expression of specific BCL family members. Pre-treatment with EPO resulted in a 6 fold increase in the expression of the anti-apoptotic gene $BCL_{XL}$ and a greater than 5 fold decrease in the expression of the pro-apoptotic Bak. These results are consistent with the gene chip results suggesting a possible mechanism for EPO's protective effects. (Bottom) Agarose gels showing RT-PCR products representing the regulation of $Bcl_{LX}$ and Bak. m—markers, 1—RT-PCR negative control, lane 2—No Treatment, lane 3—50 ng/ml NGF, lane 4—EPO 1 nm.

Pre-treatment of PC-12 cells with EPO (1 U/ml) for 24 hr resulted in significant changes in the gene expression of the bcl-2 family members $bcl_{XL}$ and bak as seen in FIG. 3. Cells treated with EPO showed a 6-fold increase in the expression of the anti-apoptotic gene, $bcl_{XL}$, and a 5-fold decrease in the expression of the pro-apoptotic gene, bak. EPO has been shown previously to increase the survival of red blood cell progenitor cells by increasing $bcl_{XL}$ expression (Silva et al., 1996). These results show that EPO uses a similar mechanism to protect neurons from undergoing apoptosis in response to injury. The regulation of bak shows that EPO can effect the expression of additional genes to elicit this effect.

EXAMPLE 3 rhEPO Neuroprotection and Neurite Outgrowth Effects on Rat Hippocampal and Cortical Cells and PC12 Cells Primary Neuronal Cell Culture Dissociated hippocampal and cortical cell cultures were established from embryonic day 18 rat fetuses as previously described (Mattson et al., 1994). Briefly, fetuses were removed via cesarean section from pregnant moms (Sprague-Dawley) anesthetized with halothane according to the AVMA Panel on Euthanasia. Pups were decapitated and the brains were removed and placed in HEPES-buffered Hank's Balanced Salt solution (HBSS; Gibco). The hippocampi and cortices were dissected out and pooled according to tissue-type. Tissue was trypsinized for 15 min (1 mg/ml trypsin-HBSS; Worthington), rinsed with fresh HBSS, incubated in trypsin inhibitor (1 mg/ml; Sigma) for 5 min, rinsed again with fresh HBSS and then triturated in 1 ml fresh HBSS with a fire-polished glass pipette. Dissociated cells were seeded at 30,000 cells/well onto poly-D-lysine coated 96-well plates (Collaborative BioScience). Each well contained 100 µl of Eagle's Minimal Essential Media (MEM; Gibco) supplemented with 26 mM $NaHCO_3$ (Sigma), 56 mM glucose (Sigma), 15 mM KCl (Sigma), 1 mM sodium pyruvate (Sigma), 1.1 mM L-glutamine (Sigma), 10% (v/v) heat-inactivated fetal bovine serum (Hyclone), and 0.001% gentamicin sulfate (Sigma) (pH 7.4). Cells were allowed to attach for 24 h in a humidified 37° C. 5% $CO_2$ incubator before experimental treatment. The culture media was aspirated and exchanged with fresh media every three days.

Glutamate Toxicity Assay

Cortical cells were seeded at 200,000 cells/dish onto polyethylenimine-coated 35 mm culture dishes. Each dish contained 1.5 ml MEM supplemented as described above. On the seventh day in culture, four fields per pre-marked dish were visualized with a Nikon Diaphot inverted microscope (10×magnification) and photographed prior to experimental treatment. Immediately following, the cultures were treated with vehicle or recombinant human erythropoietin (rhEPO; lot #41C514; 50 µM stock in 0.2M citrate, 0.585 g.L NaCl diluted to appropriate concentrations in Dulbecco's phosphate buffered saline (DPBS; Sigma)+0.1% bovine serum albumin (BSA; Sigma)). Twenty-four hours later the cultures were treated with 100 µM glutamate (Sigma). Twenty-four hours post-glutamate, the four fields from each dish were photographed again. Cell survival was measured by counting viable cells in each field pre- and post-experimental treatment. Neurons were considered viable if they had neurites that were uniform in diameter and smooth in appearance, and somata that were smooth and round to oval in shape. Data were expressed as percent of control (vehicle; mean±SD).

PC12 Cell Culture

PC-12 cells (from a rat Pheochromocytoma) were cultured on poly-D-Lysine coated tissue culture plastic in DMEM containing 10% FBS and 5% Horse serum. To induce the neuronal phenotype in PC-12 cells, serum was removed and the cells were treated with NGF (50 ng/ml). Cells were grown for 7 days in the presence of the NGF then used for experiments.

Glutamate Toxicity

PC-12 cells were cultured as described above. 24 hr prior to insult, cells were treated with rhEPO at concentrations ranging from 1 pm to 1 nm. On the day of the experiment, cells were exposed to 200 µM glutamate for 30 min. Cells were then washed 2 times with fresh media to remove the glutamate and cultured in fresh media containing NGF but no EPO. After 24 hr cells were assayed for viability using a trypan blue exclusion assay. Briefly, media was removed and the cells were incubated in 0.4% Trypan Blue for 5 min. Cells were then washed gently with PBS, then fixed with 10% formalin. Cell viability was determined by counting the total number of cells vs. the number of trypan blue positive (dead) cells.

NGF Withdrawal

PC-12 cells were cultured as described above in a 96 well poly-d-lysine coated multi-well plate and treated with rhEPO (1 pm to 10 nm) for 24 hr prior to NGF withdrawal. On the day of the experiment the cells were washed with buffer 3 times to remove NGF and then cultured in fresh media without NGF. Immediately following NGF washout cells were counted (t=0) to determine the number of living cells. Cell viability was based on morphological characteristics including phase brightness, presence of axons, and absence of blebbing. Cell counts were performed at 12 hr, 24 hr, 48 hr and 72 hr and the number of viable cells were scored.

Neurite Outgrowth Assay

Twenty-four hours after plating, cultures were treated with vehicle (PBS+0.1% BSA), 100 ng of various growth factors (brain derived neurotrophic factor (BDNF; Promega), glial-derived neurotrophic factor (GDNF; Promega), nerve growth factor (NGF; Boehringer Mannheim), basic fibroblast growth factor (bFGF; Boehringer Mannheim), insulin-like growth factor-1 (IGF-1; Boehringer Mannheim), neurotrophin-3 (NT3; Calbiochem), neurotrophin-4 (NT4; Calbiochem), ciliary neurotrophic factor (CNTF; Calbiochem), epidermal growth factor (EGF; Calbiochem), vascular endothelial growth factor (VEGF; Calbiochem)), or rhEPO (prepared same as above; 10 fM-10 nM)). Each treatment condition was run in quadruplicate or octuplicate. On the third day in culture, the media was aspirated off and replaced with fresh media and test compound. At one week in culture, the cells were fixed with 10% phosphate-buffered formalin for 15 min, then rinsed with DPBS (Sigma) and placed in blocking serum for 30 min (horse serum; 1:50 dilution in DPBS; Vector Labs). Cultures were rinsed again with DPBS and then incubated in primary antibody for 2 hr (microtubule-associated protein-2 (MAP-2) is a selective marker for dendritic processes; anti-mouse monoclonal (Chemicon); 1:1000 dilution of MAP-2 in antibody diluent (Zymed)). Negative control wells were incubated in antibody diluent alone. Background signal was determined by blank wells (cell-free) incubated with or without antibody. Cultures were rinsed again with DPBS and then placed in fluorescein for 1 hr (FITC; anti-mouse IgG; rat adsorbed; 1:50 dilution in DPBS; Vector Labs). Cultures were rinsed a final time with DPBS and then the plates were read on a Cytofluor 4000 fluorescence plate reader. Neurite outgrowth was expressed as percent change from control (vehicle; mean fluorescence±SD).

Results

Figure 4:
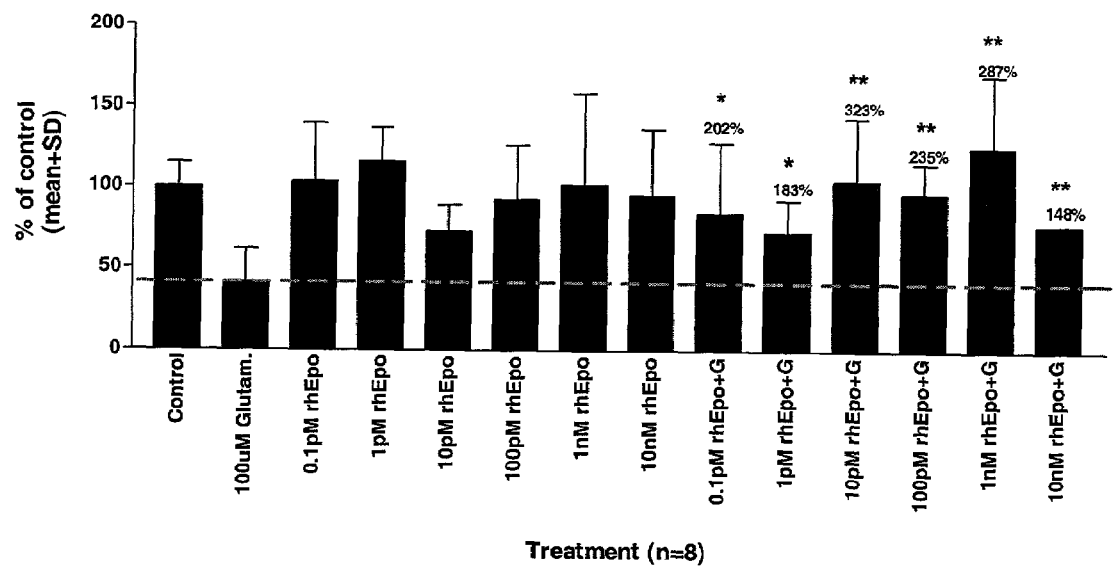
FIG. 4 shows that rhEPO protects rat cerebral cortical neurons against glutamate toxicity.

Neuroprotection study with primary neuronal cultures: Pretreatment of cultures with rhEPO for 24 h prior to glutamate administration resulted in a significant increase in neuronal survival (FIG. 4). Cell survival was maximally increased approximately 200% over parallel cultures treated with glutamate alone. The neuroprotective effect of rhEPO was concentration-dependent, with the greatest effects observed at pM concentrations in which cell survival was greater than or equal to vehicle (no glutamate) treated cultures.

Figure 5:
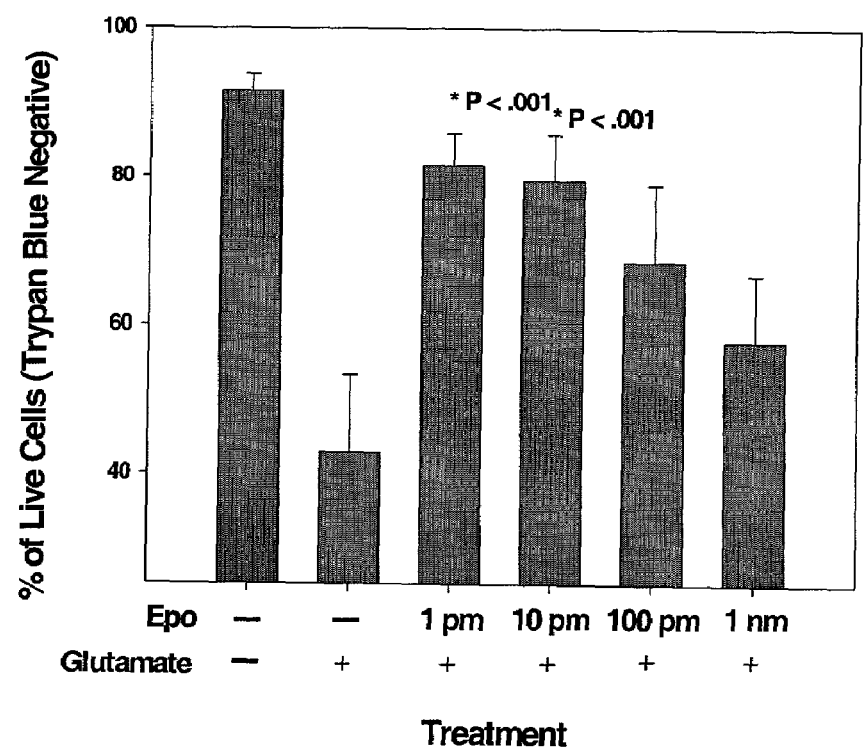
FIG. 5 shows that rhEPO protects rat PC12 cells against glutamate-induced cell death. 7 day cultures of PC-12 cells were treated with erythropoietin for 24 hours before being exposed to a toxic concentration of glutamate (200 um). Cultures were allowed to recover for 24 hours and cell survival was determined using a Trypan Blue exclusion assay. 1 to 10 pm Erythropoietin given 24 hours prior to a 15 minute exposure to glutamate significantly increased cell survival (p<0.001, student's t-test. The protective activity of EPO decreased at higher doses.
Figure 6:
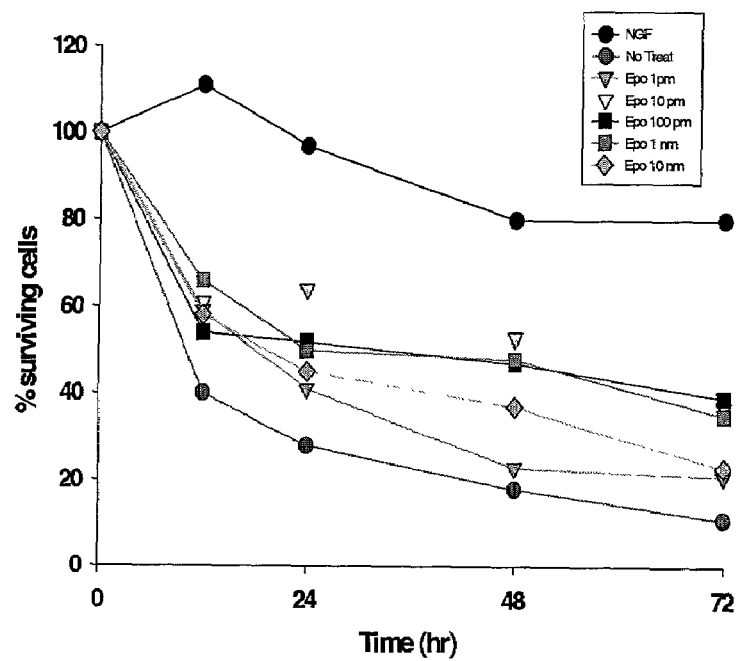
FIG. 6 shows that rhEPO protects rat PC12 cells against NGF withdrawal-induced cell death. Cultures of PC-12 cells were grown in the presence of NGF for 7 days and then treated with EPO for 24 hours before they were switched to media without NGF. Cell survival was determined by counting the number of viable cells immediately following the removal of NGF and comparing it to the number of viable cells at 12 hr, 24 hr, 48 hr and 72 hr following growth factor withdrawal. Cell viability was determined based on morphological characteristics including phase brightness, presence of axons and absence of membrane blebbing. Treatment with EPO increased the number of viable cells at each time point following growth factor withdrawal with an optimum concentration of 10 pm.
Figure 7:
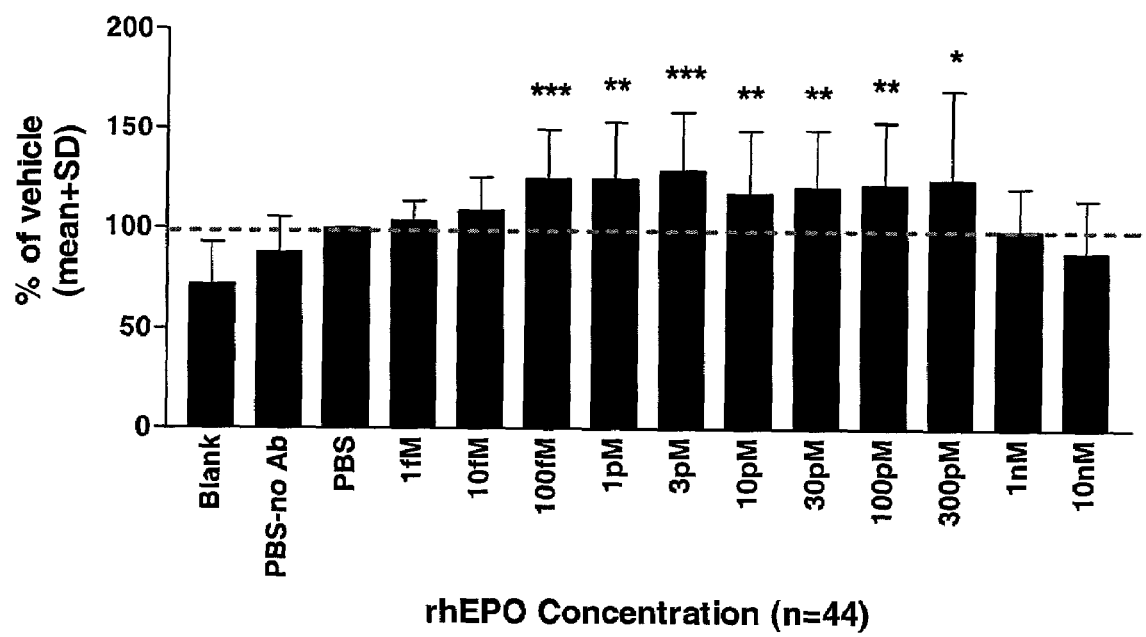
FIG. 7 shows that rhEPO promotes neurite outgrowth in rat cerebral cultures.
Figure 8:
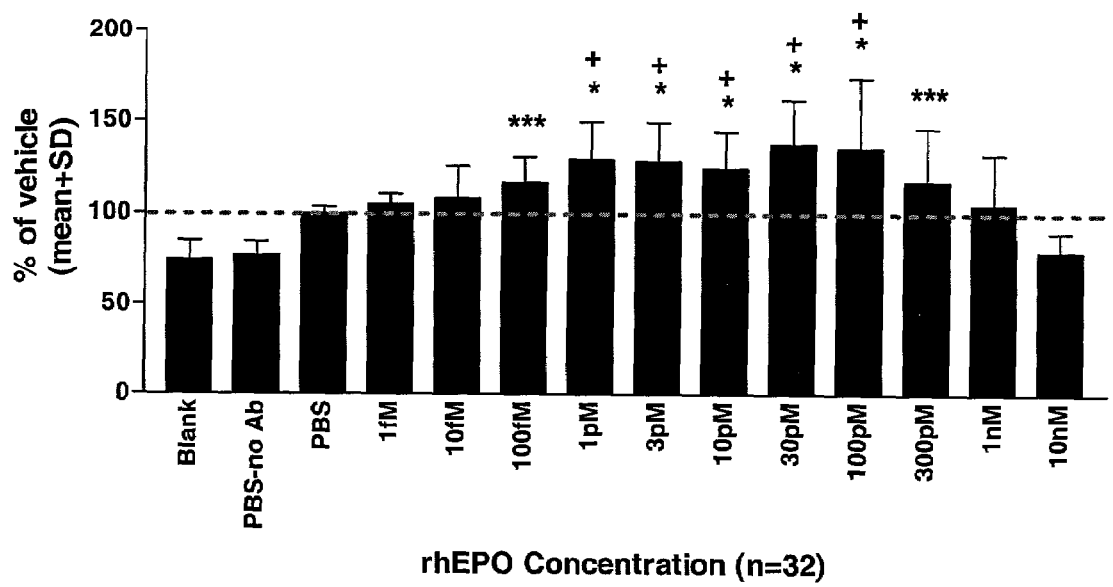
FIG. 8 shows that rhEPO promotes neurite outgrowth in rat hippocampal cultures.
Figure 9:
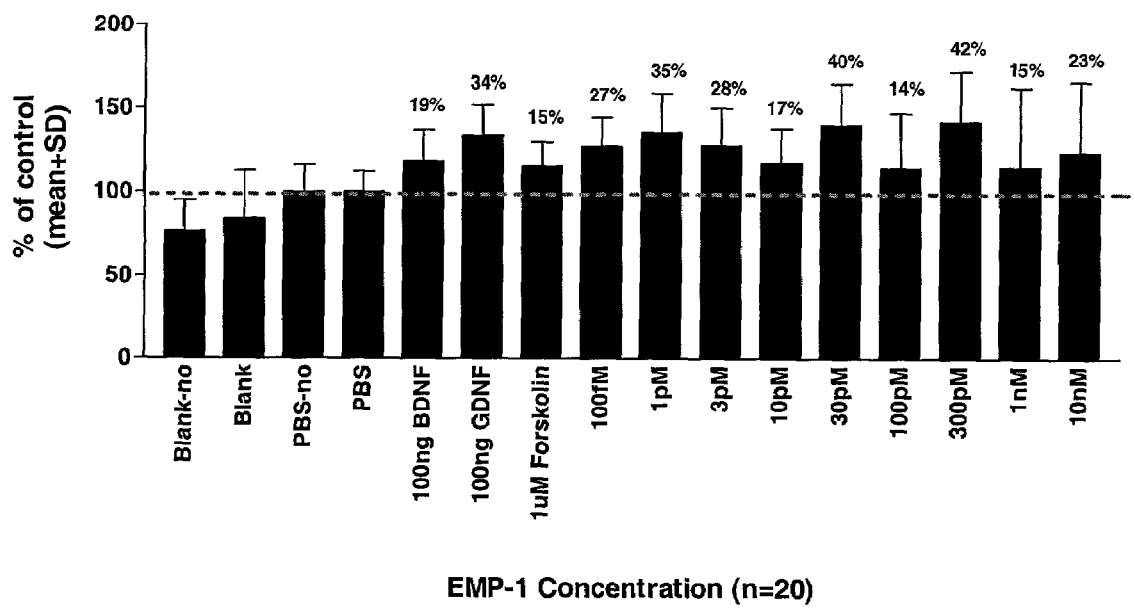
FIG. 9 shows that EMP-1 promotes neurite outgrowth in rat cerebral cortical cultures.
Figure 10:
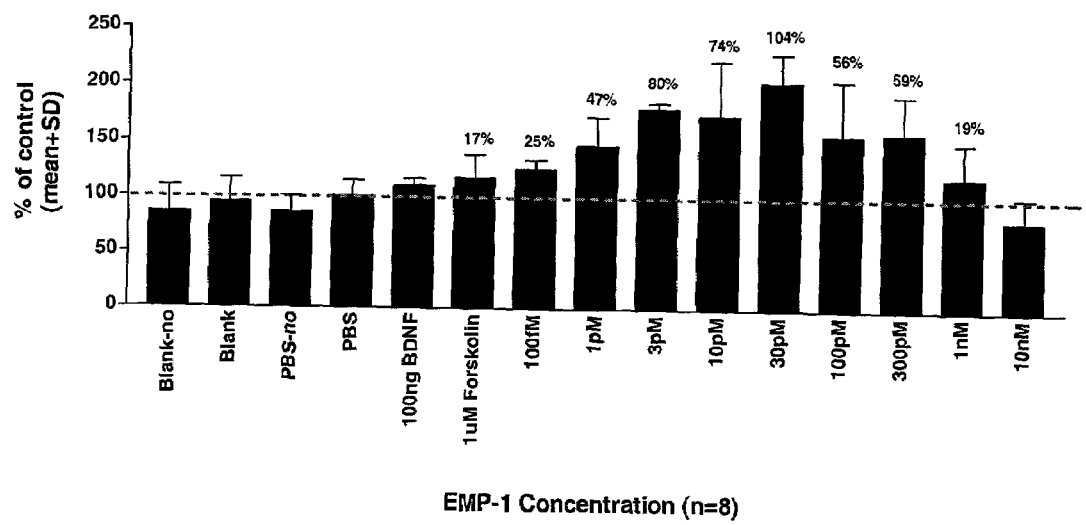
FIG. 10 shows that EMP-1 promotes neurite outgrowth in rat hippocampal cultures.
Figure 11:
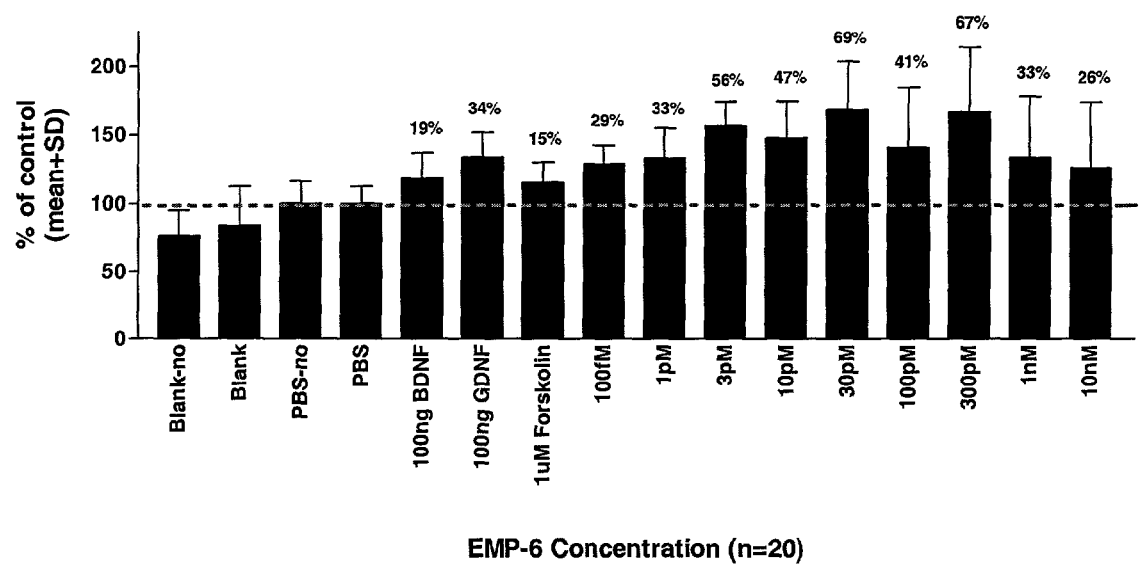
FIG. 11 shows that EMP-6 promotes neurite outgrowth in rat cerebral cortical cultures.
Figure 12:
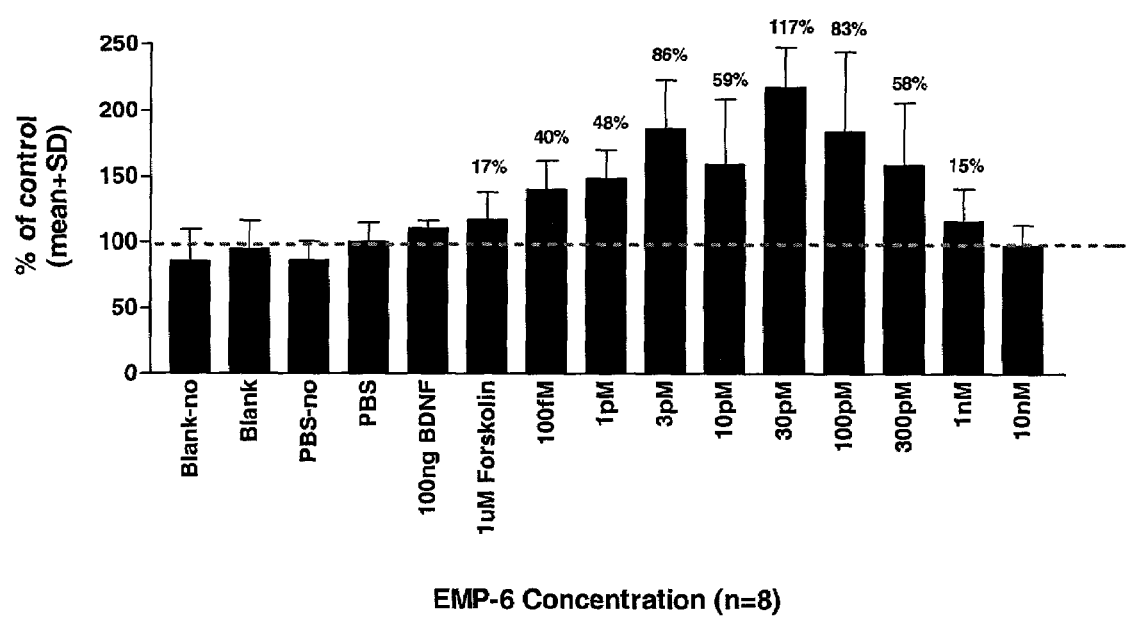
FIG. 12 shows that EMP-6 promotes neurite outgrowth in rat hippocampal cultures.
Figure 13:
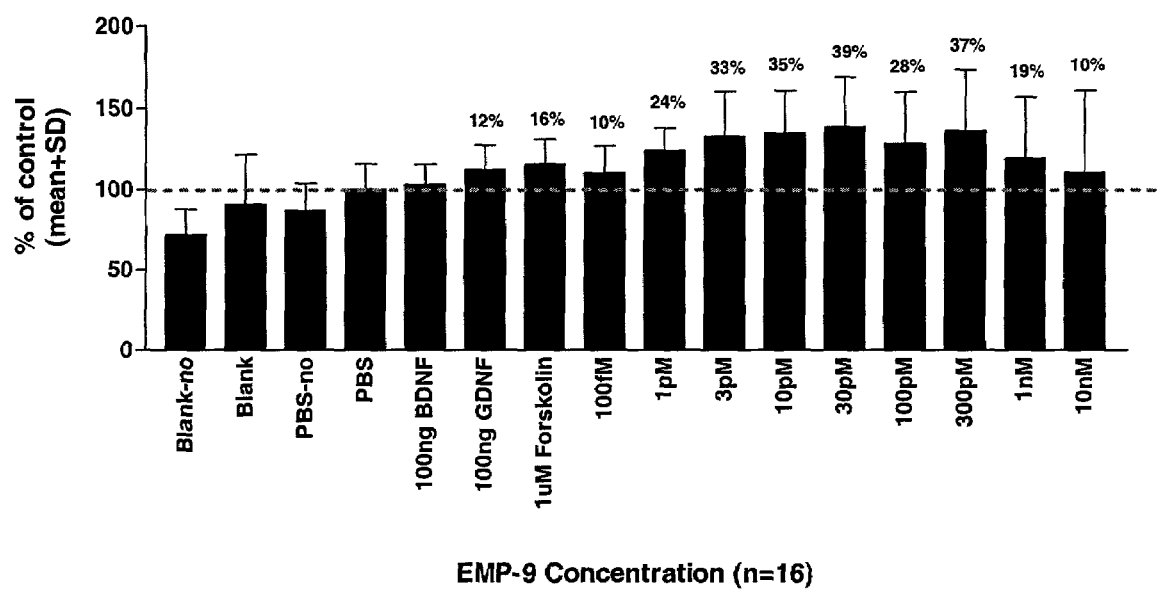
FIG. 13 shows that EMP-9 promotes neurite outgrowth in rat cerebral cortical cultures.
Figure 14:
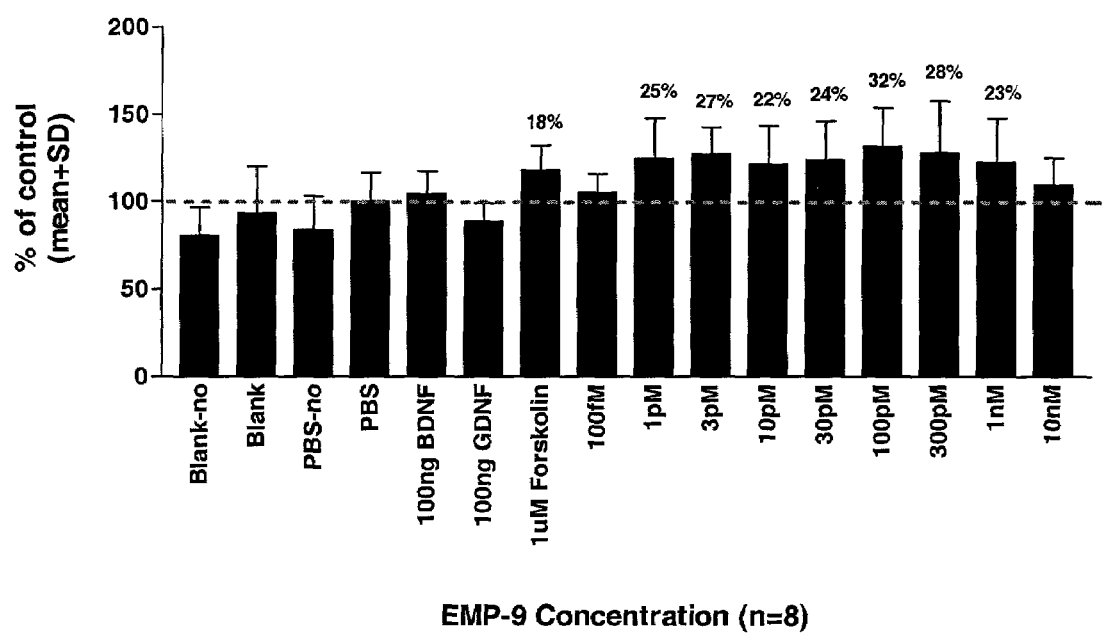
FIG. 14 shows that EMP-9 promotes neurite outgrowth in rat hippocampal cultures.
Figure 15:
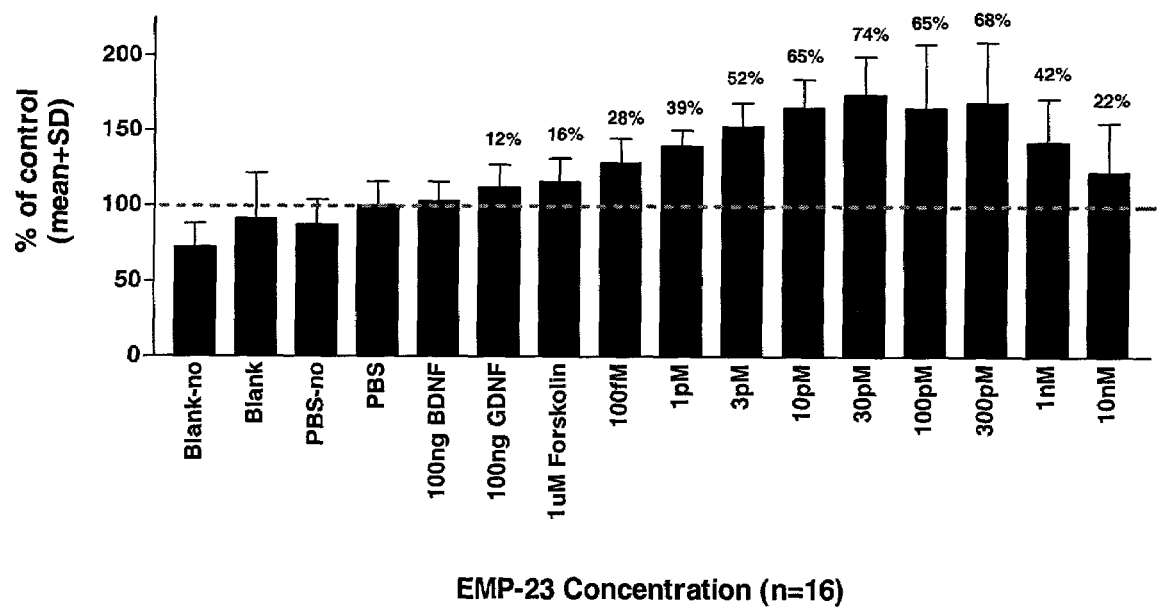
FIG. 15 shows that EMP-23 promotes neurite outgrowth in rat cerebral cortical cultures.
Figure 16:
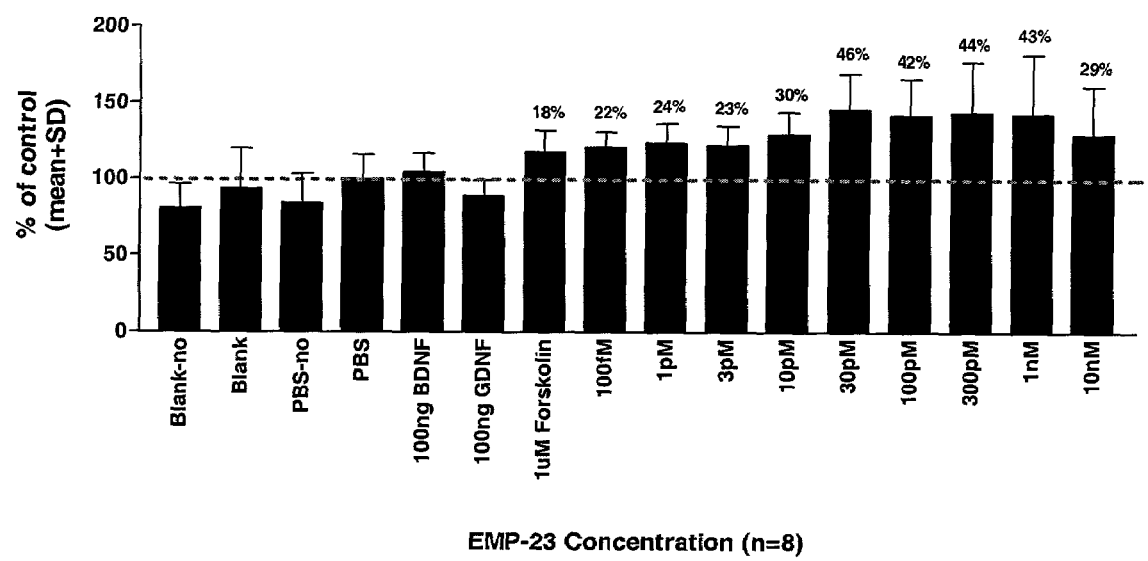
FIG. 16 shows that EMP-23 promotes neurite outgrowth in rat hippocampal cultures.
Figure 17:
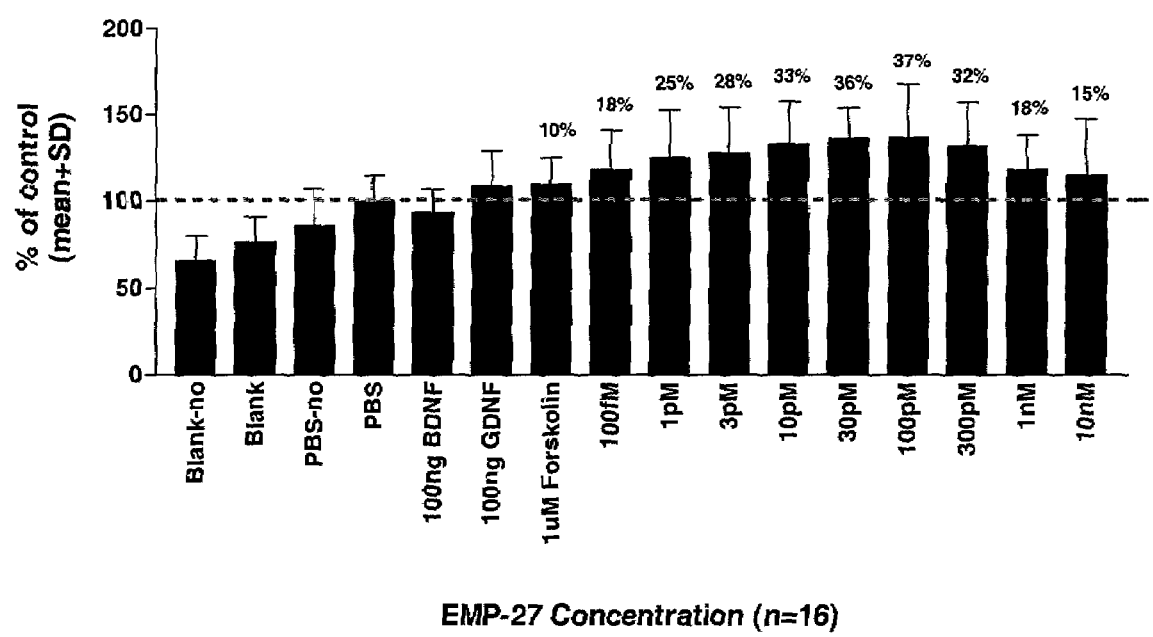
FIG. 17 shows that EMP-27 promotes neurite outgrowth in rat cerebral cortical cultures.
Figure 18:
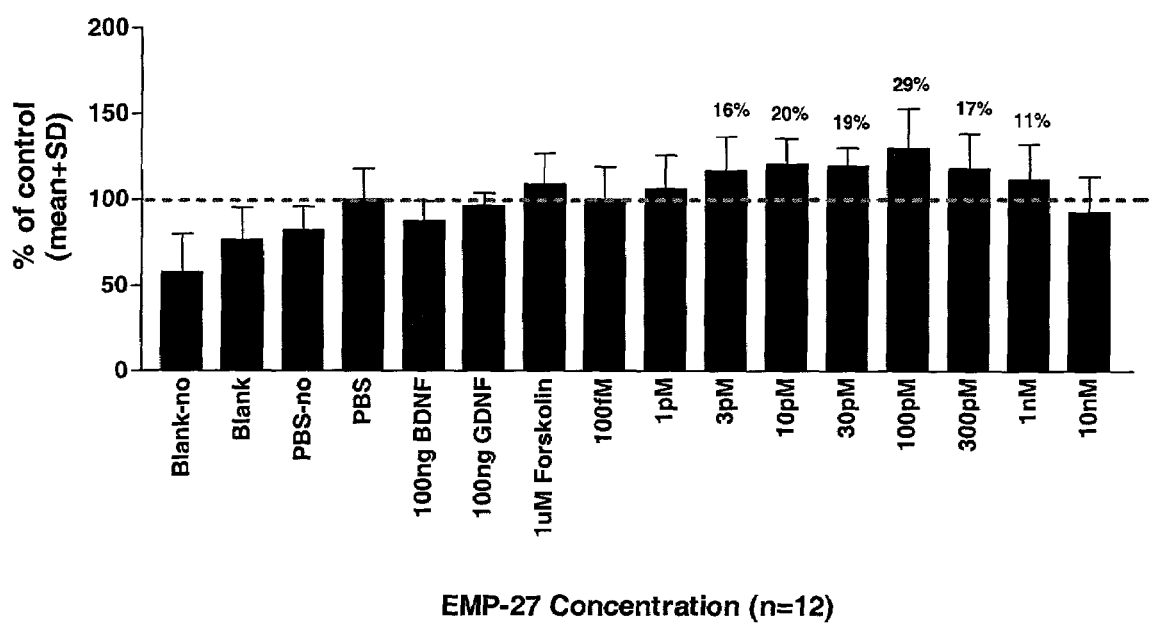
FIG. 18 shows that EMP-27 promotes neurite outgrowth in rat hippocampal cultures.

Neuroprotection study with PC12 cells: Pre-treatment with EPO resulted in a significant decrease in cell death induced by both glutamate toxicity and growth factor withdrawal in PC-12 cells (FIGS. 5 and 6). The peak concentration for the neuroprotective effect in both experiments was 10 pm. The dose response curve for the neuroprotective effect of EPO was bi-phasic with the ability of EPO to protect cells against cytotoxicity decreasing at concentrations above 10 pm, with no significant effect at 1 nm. These results suggest that EPO is able to prevent an apoptotic response in neurons exposed to a variety of cytotoxic insults Neurite outgrowth study with primary neuronal cultures: Cultures treated with rhEPO resulted in a significant increase in neurite outgrowth as measured by MAP2-FITC immunofluorescence. The neurite outgrowth promoting effect was concentration dependent with maximal activity observed at pM levels (FIGS. 7 and 8). The results indicate that rhEPO treatment induced a larger outgrowth response in the hippocampal cultures (12–44% over control) than in the cortical cultures (15–29% over control). A comparison between rhEPO and known growth factors indicates that they exhibit regional differences in their neurite outgrowth promoting abilities. rhEPO's ability to increase neurite outgrowth in cortical cultures is greater than or equal to that of known growth factors. This observation is compelling and important since few factors have such effects on cortical cells. On the other hand, many growth factors exert strong outgrowth responses in the hippocampus (38–86% over control). Compared to such growth factors, rhEPO showed moderate yet robust outgrowth promoting activity; however, its activity was superior to several growth factors including BDNF, NGF and VEGF.

Discussion

The neuroprotection studies confirmed previous evidence that rhEPO is protective at pM concentrations against glutamate toxicity and serum withdrawal in vitro.

Surprisingly we discovered that rhEPO promotes neurite outgrowth in primary mammalian neural cells. The effect was robust for hippocampal and cortical cells. The effect was potent with efficacy observed at sub-picomolar concentrations, far more potent than any previous EPO related observation. Moreover, in cerebral cortical neurons, which respond to few growth factors, rhEPO was superior in inducing neurite outgrowth relative to the majority of known growth factors.

From a therapeutic perspective, the observation that rhEPO promotes neuroprotection and neurite outgrowth in cerebral cortical neurons is very important. During neurodegeneration, neural cells can be in different stages of the process. Some may be stressed, others experience significant neurite retraction and loss of synaptic input, and eventually all affected cells will succumb to death. A therapeutic agent that can intervene in this process at multiple levels can be of great benefit to the recovery of the neural cells and eventually neural function. The present data support that rhEPO accomplishes this task by protecting the cells, by enhancing their survival, by promoting re-establishment of synaptic contacts and connections, and by stabilizing the neuronal and neural circuitry.

It should also be specified that the data are particularly important, considering that very few growth factors are effective in cerebral cortical neurons, and also that very few growth factors display the dual activity as neuroprotectants and promoters of neurite outgrowth in cortical neurons. It is particularly relevant that this dual activity of rhEPO was observed at sub-picomolar/picomolar concentrations.

EXAMPLE 4

EPO Mimetic Peptides Stimulate Neurite Outgrowth

Cell Culture

Dissociated hippocampal and cortical cell cultures were established from embryonic day 18 rat fetuses as previously described (Mattson et al., 1994). Briefly, fetuses were removed via cesarean section from pregnant moms (Sprague-Dawley) anesthetized with halothane according to the AVMA Panel on Euthanasia. Pups were decapitated and the brains were removed and placed in HEPES-buffered Hank's Balanced Salt solution (HBSS; Gibco). The hippocampi and cortices were dissected out and pooled according to tissue-type. Tissue was trypsinized for 15 min (1 mg/ml trypsin-HBSS; Worthington), rinsed with fresh HBSS, incubated in trypsin inhibitor (1 mg/ml; Sigma) for 5 min, rinsed again with fresh HBSS and then triturated in 1 ml fresh HBSS with a fire-polished glass pipette. Dissociated cells were seeded at 30,000 cells/well onto poly-D-lysine coated 96-well plates (Collaborative BioScience). Each well contained 100 µl of Eagle's Minimal Essential Media (MEM; Gibco) supplemented with 26 mM $NaHCO_3$ (Sigma), 56 mM glucose (Sigma), 15 mM KCl (Sigma), 1 mM sodium pyruvate (Sigma), 1.1 mM L-glutamine (Sigma), 10% (v/v) heat-inactivated fetal bovine serum (Hyclone), and 0.001% gentamicin sulfate (Sigma) (pH 7.4). Cells were allowed to attach for 24 h in a humidified 37° C. 5% $CO_2$ incubator before experimental treatment. The culture media was aspirated and exchanged with fresh media every 3 days.

Neurite Outgrowth Assay

Twenty-four hours after plating, cultures were treated with vehicle (PBS+0.1% BSA), 100 ng of various growth factors (brain derived neurotrophic factor (BDNF; Promega), glial-derived neurotrophic factor (GDNF; Promega), nerve growth factor (NGF; Boehringer Mannheim), basic fibroblast growth factor (bFGF; Boehringer Mannheim), insulin-like growth factor-1 (IGF-1; Boehringer Mannheim), neurotrophin-3 (NT3; Calbiochem), neurotrophin-4 (NT4; Calbiochem), ciliary neurotrophic factor (CNTF; Calbiochem), epidermal growth factor (EGF; Calbiochem), vascular endothelial growth factor (VEGF; Calbiochem)), or Epo mimetic peptides (EMP1, EMP6, EMP9, EMP23 and EMP27; diluted in DPBS+0.1% BSA; 10 fM–10 nM; Table 1). Each treatment condition was run in quadruplicate. On the third day in culture, the media was aspirated off and replaced with fresh media and test compound. At one week in culture, the cells were fixed with 10% phosphate-buffered formalin for 15 min, then rinsed with DPBS (Sigma) and placed in blocking serum for 30 min (horse serum; 1:50 dilution in DPBS; Vector Labs). Cultures were rinsed again with DPBS and then incubated in primary antibody for 2 hr (microtubule-associated protein-2 (MAP-2) is a selective marker for dendritic processes; anti-mouse monoclonal (Chemicon); 1:1000 dilution of MAP-2 in antibody diluent (Zymed)). Negative control wells were incubated in antibody diluent alone. Background signal was determined by blank wells (cell-free) incubated with or without antibody. Cultures were rinsed again with DPBS and then placed in fluorescein for 1 hr (FITC; anti-mouse IgG; rat adsorbed; 1:50 dilution in DPBS; Vector Labs). Cultures were rinsed a final time with DPBS and then the plates were read on a Cytofluor 4000 fluorescence plate reader. Neurite outgrowth was expressed as percent change from control (vehicle; mean fluorescence±SEM).

TABLE 1

Erythropoeitin Mimetic Peptides (EMP)

| SEQ.ID.NO | Sequence name | Sequence |
| --- | --- | --- |
| 8 | EMP-1 | GGTYSCHFGPLTWVCKPQGG |
| 19 | EMP-6 | GGTASCHFGPLTWVCKPQGG |
| 20 | EMP-9 | GGTYSCHFAPLTWVCKPQGG |
| 17 | EMP-23 | Y-CHFGPLTWVC |
| 21 | EMP-27 | GGTYSC-FGPLTWVCKPQGG |

Results

Neurite outgrowth study: Cultures treated with EMP's resulted in a significant increase in neurite outgrowth as measured by MAP2-FITC immunofluorescence. The neurite outgrowth promoting effect was concentration dependent with maximal activity observed at pM levels (FIGS. 9–18). The results indicate that EMP's displayed different activity profiles. At the concentrations tested, EMP-1 and 6 displayed typical bell-shaped dose-response profiles in hippocampal cultures with peak activity observed between 30–300 pM (83–117% increase over vehicle). EMP-9 and 27 exhibited a flat response profile in hippocampal cultures with peak activity observed at similar concentrations as EMP-1 and 6, but the amplitude of the response was greatly attenuated (29–32% increase over vehicle). EMP-23 had a modest response to EPO in hippocampal cultures with peak activity observed between 30 pM-1 nM that led to a 43–46% increase over vehicle response. In the cortical cultures, EMP-1, 9 and 27 exhibited response profiles similar to most known growth factors—a flat response overall with maximal activity occurring between 30–300 pM reaching 32–40% above the vehicle response. EMP-6 and 23 displayed typical bell-shaped dose-response profiles with peak activity observed between 30–300 pM resulting in a 68–87% increase in outgrowth over vehicle response levels. Overall, EMP-6 promoted robust neurite outgrowth activity in both hippocampal and cortical cultures; whereas, EMP-1 showed selective effects in hippocampal cultures over cortical cultures and EMP-23 effects were greater in cortical cultures than hippocampal cells. EMP-9 and 27 neurite outgrowth responses were less impressive overall.

A comparison between the EMP's and known growth factors indicated that they exhibit regional differences in their neurite outgrowth promoting abilities. The EMP's ability to increase neurite outgrowth in cortical cultures was greater than or equal to that of known growth factors (FIGS. 9–18). This observation is compelling and important since few factors have such effects on cortical cells. On the other hand, many growth factors exert strong outgrowth responses in the hippocampus (38–86% over control). Compared to such growth factors, the EMP's showed moderate yet robust outgrowth promoting activity; however, they displayed superior activity over BDNF, NGF and VEGF.

Discussion

EMP's promote neurite outgrowth in mammalian cells. The effect was robust for hippocampal and cortical cells. The neurite outgrowth promoting effect was superior to that of various growth factors. The effect was potent with efficacy observed at picomolar concentrations.

It should also be specified that the data are particularly important, considering that very few growth factors or mimetics are effective in cerebral cortical neurons in promoting neurite outgrowth. It is particularly relevant that this activity of the EMPs was observed at sub-picomolar/picomolar concentrations.

EXAMPLE 5

EPO Protects Against Ischemic Injury

Subjects

Male spontaneous hypertensive rats (Charles River) weighing between 250–300 g were weighed and then anesthetized with ketamine (100 mg/ml)/xylazine (20 mg/ml) cocktail (1.2 ml/kg; i.p.). The level of anesthetic was assessed by corneal reflex (air puff to eye) and leg jerk in response to tail or foot pinch. Once the rat was anesthetized, it was placed on a small animal surgical board and restrained during the surgical procedure. The rat's body temperature was monitored continuously with a rectal probe and maintained at 37° C. with a homeostatic heating pad.

Experimental Model of Cerebral Ischemia

Rats were rendered ischemic by tandem occlusion of the left common carotid artery and the left middle cerebral artery for 2 h followed by 22 h of reperfusion using a modification of the technique described by Brint and coworkers (*J. Cereb Blood Flow Metab* 8:474–485, 1988). Specifically, the left CCA was isolated through an incision in the ventral surface of the neck. For isolation of the ipsilateral MCA, a second incision was made between the lateral canthus of the left eye and the corresponding external auditory canal to bare the underlying skull. The MCA was exposed through a 5 mm burrhole drilled 2–3 mm rostral to the fusion of the zygomatic arch and the squamosal bone under direct visualization with a Zeiss operating microscope. The dura was opened with a sterile 26 g needle and a platinum alloy wire (0.1 mm diameter) was inserted beneath the MCA just superior to the inferior cortical vein. The MCA was temporarily occluded by elevation and compression of the vessel across the alloy wire, as described by Aronowski and colleagues (*Stroke,* 25:2235–2240, 1994). Concurrently, the CCA was occluded with an aneurysm clip. The duration of occlusion of the CCA and the MCA was 2 h. At the end of this period, the wire and the clip were carefully removed to allow reperfusion of the vessels and the incision area was sutured shut. The rat was placed in an isolation cage to recover before returning to his home cage.

Study Design

Study I: EPO and Vehicle Delivered Via Osmotic Mini-Pump

Twenty-hours prior to the onset of ischemia, an osmotic mini-pump (Model 1003D; Alza) filled with vehicle or EPO was placed between the scapula of the rat. A catheter attached to the pump was inserted and tethered within the right jugular vein for continuous infusion of drug at a rate of 1 μl/hr. Rats were divided into five groups: (1) sham-operated vehicle-treated, (2) ischemic vehicle treated, (3) ischemic 1.32 U/day EPO treated, (4) ischemic 132 U/day EPO treated and (5) ischemic 1321 U/day EPO treated. On Day Two, rats were rendered ischemic as described above. Twenty-two hours later, the rats were evaluated for behavioral performance, a blood sample was collected for terminal plasma levels of EPO and then the rat was euthanized, brain removed, sectioned and stained for histological analysis.

Study II: EPO and Vehicle Delivered as a Single Intravenous Bolus Injection

On Day One, the rats were rendered ischemic as described above. Rats were divided into four groups: (1) ischemic vehicle treated, (2) ischemic 1000 U/kg EPO treated, (3) ischemic 2500 U/kg EPO treated and (4) 5000 U/kg EPO treated. Fifteen minutes post-occlusion, the rats received vehicle or EPO as an intravenous bolus injection. Twenty-two hours later, the rats were evaluated for behavioral performance, a blood sample was collected for terminal plasma levels of EPO and then the rat was euthanized, brain removed, sectioned and stained for histological analysis.

Study III: EPO and Vehicle Delivered as Repeat Intravenous Bolus Injections

On Day One, the rats were rendered ischemic as described above. Rats were divided into two groups: (1) ischemic vehicle treated and (2) ischemic 2500 U/kg EPO treated. Drug was administered as an intravenous bolus at 15 min, 2 h, 4 h and 6 h post-occlusion for a total dose of 10,000 U/kg. Twenty-two hours later, the rats were evaluated for behavioral performance, a blood sample was collected for terminal plasma levels of EPO and then the rat was euthanized, brain removed, sectioned and stained for histological analysis.

Outcome Measures

Plasma Determinations: Blood samples were collected from each rat via the orbital sinus at the time of sacrifice.

Plasma was separated out, frozen and analyzed by EPO ELISA for determination of plasma concentration (U/ml).

Infarct Volume: Brains were removed, blocked into 1 mm slabs and stained with 2,3,5-triphenyl tetrazolium chloride dye (TTC; Sigma) for 15 min at room temperature. Stained sections were stored in 10% buffered formalin at 4° C. Sections were visualized by a Nikon SMZ-U microdissecting scope. Images of each brain section were captured with a CCD camera and processed using Image Pro Phase III software in order to calculate infarct volume.

Results

Figure 19:
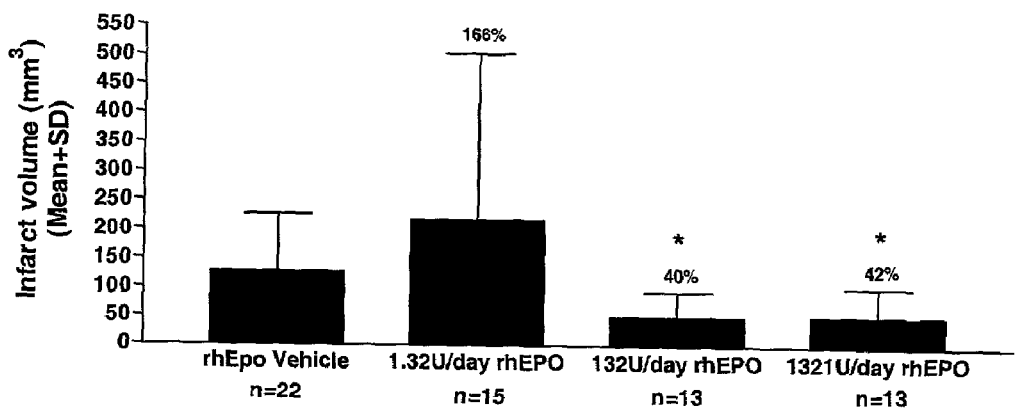
FIG. 19 shows that EPO protects against ischemic injury: study I continuous iv infusion via osmotic mini-pump.
Figure 20:
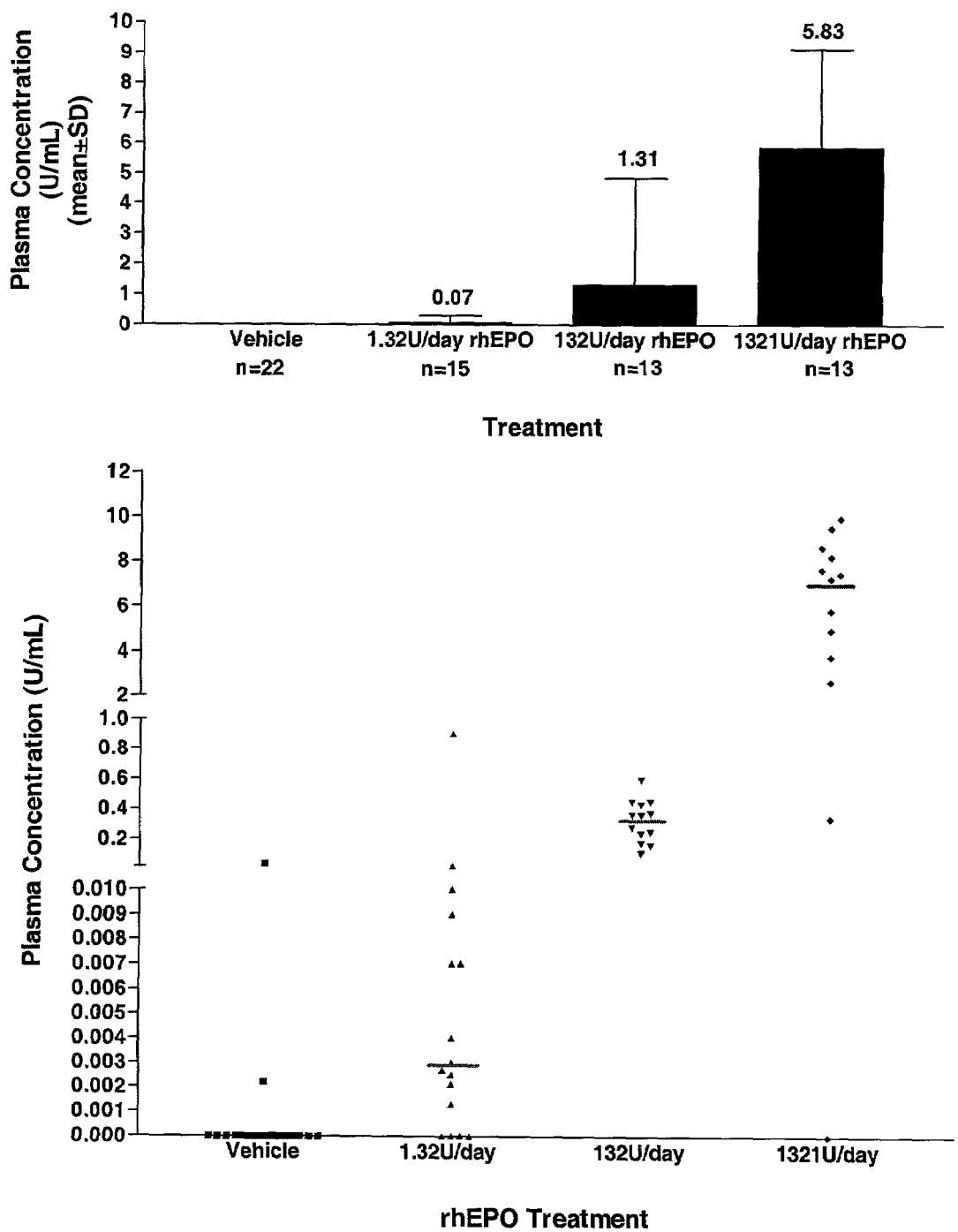
FIG. 20 shows plasma determinations for study I.

Study I: EPO given at 132 or 1321 U/day as a continuous infusion via osmotic mini-pump significantly reduced infarct volume (FIG. 19). Plasma concentrations correlated with the protective effect (FIG. 20).

Figure 21:
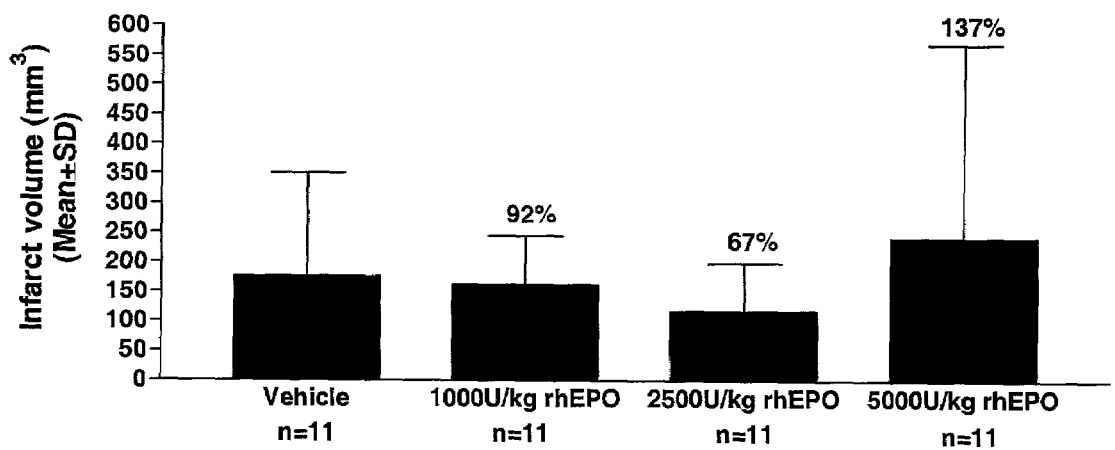
FIG. 21 shows that EPO does not protect against ischemic injury: study II single iv bolus dose.
Figure 22:
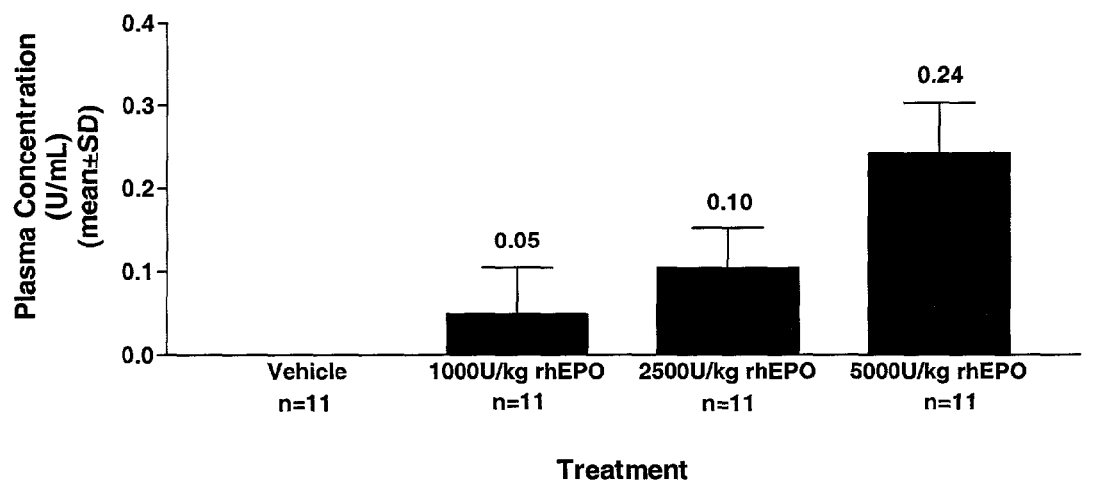
FIG. 22 shows plasma determinations for study II.
Figure 22:
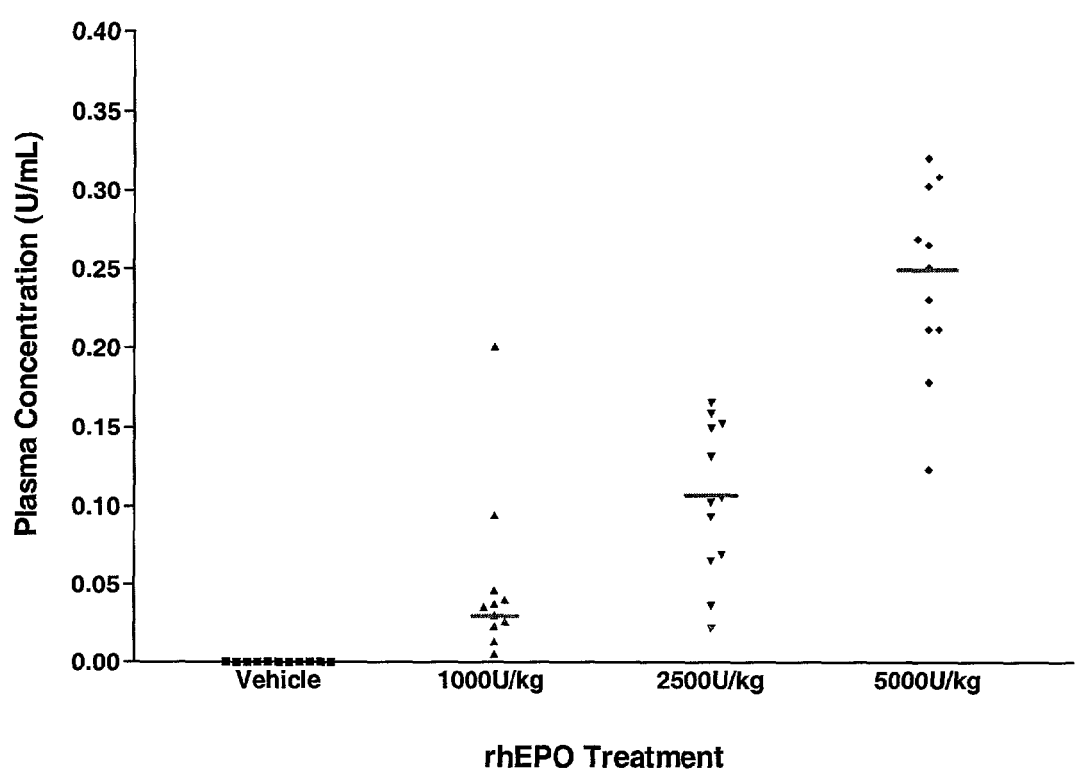

Study II: EPO given as a single iv bolus 15 min post-occlusion did not protect against ischemic damage in this model at 1000, 2500 or 5000 U/kg (FIG. 21). Plasma concentrations were low in each group (FIG. 22).

Figure 23:
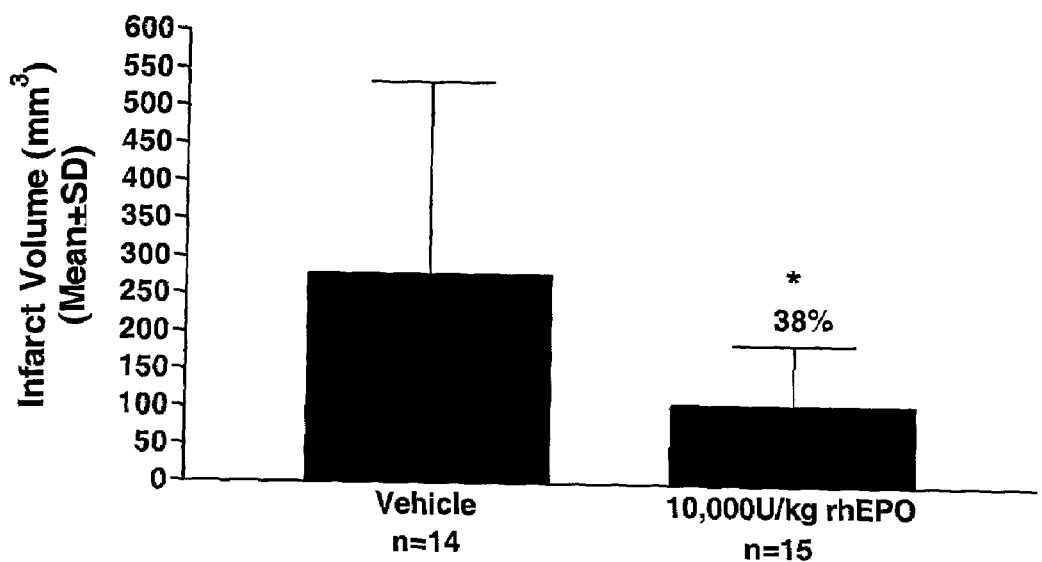
FIG. 23 shows that EPO protects against ischemic injury: study III repeat iv bolus dosing.
Figure 24:
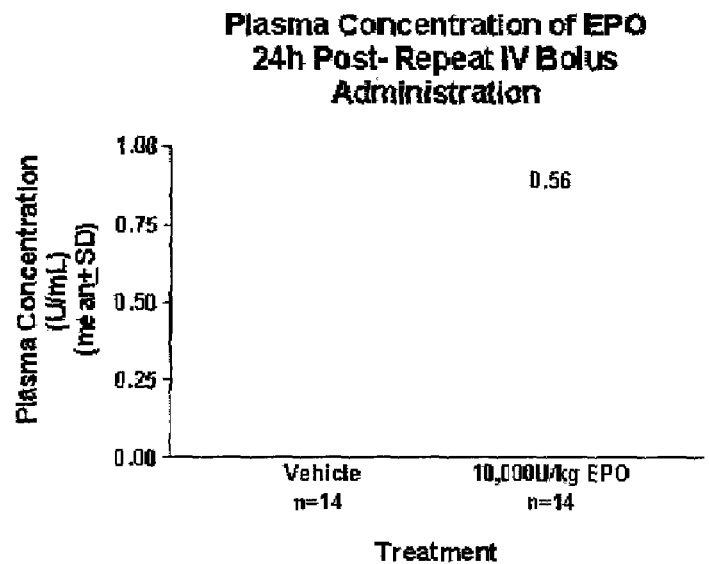
FIG. 24 shows plasma determinations: study III.

Study III: EPO given as a repeat iv bolus of 2500 U/kg at 15 min, 2 h, 4 h and 6 h post-occlusion led to a significant decrease in infarct volume (FIG. 23). Plasma concentrations are presently being determined (FIG. 24).

Discussion

Data support that continuous or repeat dosing with low to moderate concentrations of EPO can significantly reduce infarct volume in spontaneous hypertensive rats rendered ischemic via the transient tandem occlusion of the CCA and MCA. The results also support that there is a critical relationship between the amount and timing of EPO administration for the protective effect to occur. Low doses of EPO given over an extended period of time can be more beneficial than high doses given the same way or as a single bolus infusion. This is in agreement with the in vitro data indicating that EPO maximal protective effect is observed at low doses (pM) and actually looses efficacy at higher doses (μM).

REFERENCES

Johnson, D. L., Farrell, F. X., Barbone, F. P., McMahon, F. J., Tullai, J., Hoey K., Wrighton, N. C., Livnah, O., Middleton, S. A., Loughney, D., Stura, E. A., Dower, W. J., Mulcahy, L. S., Wilson, I. A. & Jolliffe L. K., Identification of a 13 Amino Acid Peptide Mimetic of Erythropoietin and Description of Amino Acids Critical for the Mimetic Activity of EMP1, Biochemistry 37, 3699–3710 (1998).

Johnson, D. L., Farrell, F. X., Barbone, F. P., McMahon, F. P., Tullai, J., Kroon, D., Freedy, J., Zivin, R. A., Mulcahy, L. S., & Jolliffe, L. K. Amino Terminal Dimerization of an Erythropoietin Mimetic Peptide Results in Increased Erythropoietic Activity, Chemistry & Biology 4, 939–950 (1997).

Johnson, Dana L.; Zivin, Robert A. Agonist peptide dimers. U.S. Pat. No. 5,767,078

Campana, W. M., Misasi, R. and O'Brien, J. S. (1998) Identification of a neurotrophic sequence of erythropoietin. Inter. J. Mol. Med. 1:235–241.

Patent application WO 95/03821, O'Brien, J. S., Kishimoto, Y. and Altman, D. E. Title: Prosaposin and cytokine-derived peptides as therapeutic agents.

Sadamoto, Y, Igase, K, Sakanaka, M., Sato, K, Otsuka, H., Sakaki, S., Masuda, S. and Sasaki, R. (1998). Erythropoietin prevent place navigation disability and cortical infarction in rats with permanent occlusion of the middle cerebral artery. Biochem Biophys Res Comm. 253:26–32.

Tabira, T., Konishi, Y. and Gallyas, F. (1995). Neurotrophic effect of hematopoietic cytokines on cholinergic and other neurons in vitro. Int. J. Dev. Neurosci. 13:241–252.

Morishita, E., Masuda, S., Nagao, M., Yasuda, Y. and Sasaki, R. (1997). Erythropoietin receptor is expressed in rat hippocampal and cerebral cortical neurons, and erythropoietin prevent in vitro glutamate-induced neuronal death. Neurosci 76:105–116.

Sakanaka, M, Wen T -C, Matsuda, S, Masuda, S., Morishita, E., Nagao, M., and Sasaki, R. (1998) In vivo evidence that erythropoietin protects neurons from ischemic damage. Proc. Natl. Acad. Sci. 95:4635–4640.

Marti, H. H., Gassman, M., Wenger, R. H., Kvietikova, I., Morganti-Kossmann, M. C., Kossmann, T., Trentz, O., and Bauer, C. (1997) Detection of erythropoietin in human liquor: Intrisic erythropoietin production in the brain. Kidney Int. 51:416–418.

Konishi, Y., Chui, D -H, Hirose, H., Kunishita, T. and Tabira, T. (1993) Trophic effect of erythropoietin and other hematopoietic factors on central cholinergic neurons in vitro and in vivo. Brain Res. 609:29–35.

Bernaudin, M., Marti, H. H., Roussel, S., Divoux, D., Nouvelot, A., MacKenzie, E. T. and Petit, E. (1999). A potential role for erythropoietin in focal permanent cerebral ischemia in mice. J. Cereb. Blood Flow Metab. 19:643–51.

Nakamura, T., Ebihara, I., Shimada, N. and Koide, H. (1998) Elevated levels of erythropoietin in cerbrospinal fluid of depressed patients. Amer. J Med Sci 315:199–201.

Masuda, S., Okano, M., Yamagishi, K., Nagao, M., Ueda, M. and Sasaki, R. (1994) A novel site of erythropoietin production. Oxygen-dependent production in cultured rat astrocytes. J. Biol. Chem. 269:19488–93.

Patent application WO 98-CA991, Weiss, S and Sorokan, S. T. Title: Erythropoietin-mediated neurogenesis.

Campana, W. M., Misasi, R. and O'Brien, J. S. (1998) Identification of a neurotrophic sequence of erythropoietin. Inter. J. Mol. Med. 1:235–241.

Patent application: WO 95/03821, O'Brien, J. S., Kishimoto, Y. and Altman, D. E. Title: Prosaposin and cytokine-derived peptides as therapeutic agents.

Konishi, Y., Chui, D -H, Hirose, H., Kunishita, T. and Tabira, T. (1993) Trophic effect of erythropoietin and other hematopoietic factors on central cholinergic neurons in vitro and in vivo. Brain Res. 609:29–35.

Mattson, M. P., Barger, S. W., Begley, J, and Mark, R. J. (1994) Calcium, free radicals and excitotoxic neuronal death in primary cell culture. Methods Cell Biol. 46:187–216.

Smith-Swintosky V L, Cheo-Isaacs C T, D'Andrea M R, Santulli R J, Darrow, A L, Andrade-Gordon P. (1997) Protease-activated receptor 2 (PAR-2) is present in the rat hippocampus and is associated with neurodegeneration. J. Neurochem., 69:1890–1896.

Silva, M., Grillot, D., Benito, A., Richard, C., Nunez, G., Fernandez-Luna, J. L. (1996). Erythropoietin can promote erythroid progenitor survival by repressing apoptosis through $Bcl-x_L$ and Bcl-2. Blood 88, pp1576–1582.

What is claimed is:

1. A method for promoting neurite outgrowth in a cell culture, comprising administering to said cell culture an effective amount of one or more monomeric peptides, selected from the group consisting of:
GGTYSCHFGPLTWVCKPQGG (SEQ ID NO:8);
GGTASCHFGPLTWVCKPQGG (SEQ ID NO:19);
GGTYSCHFAPLTWVCKPQGG (SEQ ID NO:20);
GGTYSCFGPLTWVCKPQGG (SEQ ID NO:21); and,
YCHFGPLTWVC (SEQ ID NO:17).

2. The method of claim 1, wherein each of said monomeric peptides is independently selected from:
GGTASCHFGPLTWVCKPQGG (SEQ ID NO 19);
GGTYSCHFAPLTWVCKPQGG (SEQ ID NO:20);
GGTYSCFGPLTWVCKPQGG (SEQ ID NO:21);
YCHFGPLTWVC (SEQ ID NO:17).

3. The method of claim 1, wherein the cell culture comprises cortical cells.

4. The method of claim 1, wherein the cell culture comprises hippocampal cells.

* * * * *